(12) United States Patent
Schellenberger et al.

(10) Patent No.: US 9,139,843 B2
(45) Date of Patent: Sep. 22, 2015

(54) ENDOTOXINS HAVING NEMATOCIDAL ACTIVITY AND METHODS OF USE THEREOF

(75) Inventors: Ute Schellenberger, Palo Alto, CA (US); Jun-Zhi Wei, Palo Alto, CA (US); Genhai Zhu, San Jose, CA (US)

(73) Assignee: PIONEER HI BRED INTERNATIONAL INC, Johnston, IA (US)

( * ) Notice: Subject to any disclaimer, the term of this patent is extended or adjusted under 35 U.S.C. 154(b) by 594 days.

(21) Appl. No.: 13/478,515

(22) Filed: May 23, 2012

(65) Prior Publication Data

US 2012/0304337 A1 Nov. 29, 2012

Related U.S. Application Data

(60) Provisional application No. 61/489,463, filed on May 24, 2011.

(51) Int. Cl.
| | |
|---|---|
| *A01H 5/00* | (2006.01) |
| *C12N 15/82* | (2006.01) |
| *C07K 14/325* | (2006.01) |
| *A01N 25/00* | (2006.01) |
| *A01H 5/10* | (2006.01) |
| *C12N 1/21* | (2006.01) |
| *C12N 15/32* | (2006.01) |
| *C07K 14/66* | (2006.01) |
| *A01N 63/02* | (2006.01) |

(52) U.S. Cl.
CPC ............ *C12N 15/8285* (2013.01); *A01N 63/02* (2013.01); *C07K 14/325* (2013.01); *C07K 14/66* (2013.01)

(58) Field of Classification Search
None
See application file for complete search history.

(56) References Cited

U.S. PATENT DOCUMENTS

2007/0294787 A1* 12/2007 Carozzi et al. ............... 800/279
2010/0024075 A1* 1/2010 Aroian et al. ............... 800/301

FOREIGN PATENT DOCUMENTS

WO 94/16079 A2 7/1994

OTHER PUBLICATIONS de Maagd et al, (1999), Appl. Environ. Microbiol. vol. 65 pp. 4369-4374.*
Tounsi et al, (2003) J. Appl. Microbiol. vol. 95 pp. 23-28.*
Angsuthanasombat et al, (2001) J. Biochem. Mol. Biol. vol. 34 pp. 402-407.*
Aaronson et al, (2001), FEMS Microbiol. Lett. vol. 195 pp. 1-8.*
Guo et al (2004, Proc. Natl. Acad. Sci. USA vol. 101 pp. 9205-9210.* Accession Q45710.
Wei, Jun-Zhi et al; "*Bacillus thuringiensis* crystal proteins that target nematodes", Proceedings of the National Academy of Sciences, vol. 100 (9); 2760-2765 (2003).
Li, Xiang-Qian et al; "Resistance to root-knot nematode in tomato roots expressing a nematicidal *Bacillus thuringiensis* crystal protein", Plant Biotech Journal,vol. 5; 455-464 (2007).
Griffitts, Joel S. et al; "Glycolipids as Receptors for *Bacillus thuringiensis* Crystal Toxin"; Science Magazine, vol. 307; 922-925 (2005).
Griffitts, Joel S. et al; "Bt Toxin Resistance from Loss of a Putative Carbohydrate-Modifying Enzyme"; Science Magazine, vol. 293; 860-864 (2001).

* cited by examiner

*Primary Examiner* — Amjad Abraham
*Assistant Examiner* — Ryan H Brown
(74) *Attorney, Agent, or Firm* — Pioneer Hi Bred Int'l

(57) ABSTRACT

The invention provides novel δ-endotoxin polypeptides, and variants and fragments thereof, obtained from *Bacillus thuringiensis* having pesticidal activity against nematodes. Particular embodiments of the invention provide isolated nucleic acids encoding pesticidal proteins, biopesticide compositions, expression cassettes, and transformed microorganisms and plants comprising a nucleic acid of the invention. These compositions find use in methods for controlling pests, especially plant parasitic nematodes.

10 Claims, 7 Drawing Sheets

Figure 1a

MRMDCNLQSQQNIPYNVLAIPVSNVNALVDTAKDLKEAWEAFQKTGSFSLTALQQGFSASQGGAF
NYLTLLQSGISLAGSFVPGGTFVAPIVNMVIGWLWPHKNKTADTENLIKLIDEEIQKQLNKALLE
QDKNNWTSFLESIFDVSNTVSNAMIDAQWSGTVDTTNRQPKTPTTSDYLNVVGKFDSADSAIVTN
ENQIMNGNFDVAASPYFVIGATLRLSLFQSYIKFCNNWIDAVGFNPSDSNTQKANLARMKQTMRI
TINEYTQRIMKVFKDPKNMPTIGTNKFSVDAYNVYVKGMTLNVLDMVAIWPSLYPNDYTSQTTLE
QTRVTFSNMVGQEEGTDGTLKIYNTFDSSSFQHSLIPNNNVDLISYFNDELQNLELAVYTPPKKD
SGYSYPYGFVLKYANSKYKYGDSNDPESLGGLSTLSAPIQQINAATQNSKYLDGETINGIGASLP
GYCTTGCSATEQPFSCTSNANSYKSSCNPSDTNQKINALYAFTQTNVKGNTGKLGVLASLVPYDL
NPKNVFGELDSDTNNVILKGIPAEKGYFSNNARPTVVKEWINGASAVPLYSGNTLFMTATNLTAT
QYKIRIRYANPNSDTQIGVRITQNGSLISNSNPPLYSTTDSSMSSNLPQNVYVTGENGNYTLLDL
YSTNNVLSTGDITLQLTGGNQKIFIDRIEFIPTMPVPAATNNNNGDNDPPPIHHGCAIAGTQQLC
AGPPKFEQVSDLEKITTQVYMLFKSSLYEELDPKVSSYQINQVALKVMALSNEKFCEEKRLLRKL
VNKANQLLEARNLLVGGNFETTQNWVLGTNAYINYDSFLFNGNYLSLQPASGFFTSYAYQKIDES
TLKPYTRYKVSGFIGQSNQVELIISRYGKEIDKILNVPYAGPLPITADASITCCAPEIDQCDGGQ
SDSHFFNYSIDVGALHPELNPGIEIGLKIVQSNGNITISNLEIIEERPLTEMEIQTVNRKDQKWK
REKLLECASISELLQPIINQIDSLFKDANWYNDILPHVTYQTLKNIIVPDLPKLKHWFIDDLPGE
YYEIEQKMKEALKHAFTQLDEKNLIYNGDFTTNLIDWQIEGDARMKVLENNALALQLSNWDSSVS
QSIDILEFDEDKAYKLRVYAQGSGTIQFGNCEDEAIQFNTNSFVYKEKIIYFDTPSINLHIQSEG
PEFVVSSIDLVELSDDE (SEQ ID NO:1)

Figure 1b

```
ATGCGAATGGATTGTAATTTACAATCACAACAAAATATTCCTTATAATGTATTAGCAATACCAGTATCTAATGTT
AATGCGTTGGTTGATACAGCTAAAGATTTAAAAGAAGCATGGGAAGCATTTCAAAAAACTGGTTCTTTTTCATTA
ACAGCTTTACAACAAGGATTTTCTGCCTCACAAGGAGGAGCATTCAATTATTTAACATTATTACAATCAGGAATA
TCATTAGCTGGTTCTTTTGTCCCTGGAGGTACTTTTGTAGCACCCATTGTTAATATGGTTATTGGTTGGTTATGG
CCACATAAAAACAAGACAGCGGATACAGAAAATTTAATAAAATTAATTGATGAAGAAATTCAAAACAATTAAAC
AAAGCCTTATTAGAGCAAGATAAAAACAATTGGACCTCTTTTTTAGAAAGTATATTTGATGTTTCAAATACAGTA
AGTAATGCAATGATAGATGCTCAGTGGTCAGGTACTGTAGATACTACAAATAGACAACCAAAAACTCCAACAACA
TCAGATTATCTAAATGTTGTTGGAAAATTTGATTCAGCGGATTCTGCAATTGTAACTAATGAAAATCAAATAATG
AACGGCAACTTTGACGTAGCTGCATCACCCTATTTTGTTATAGGAGCAACATTACGTCTTTCATTATTTCAATCT
TATATTAAATTTTGTAATAATTGGATTGATGCAGTTGGATTTAATCCATCAGATTCTAATACACAAAAGGCTAAT
TTAGCTCGTATGAAACAAACTATGCGTATTACAATTAACGAGTATACACAAAGAATTATGAAAGTTTTTAAAGAT
CCCAAGAATATGCCTACAATAGGTACTAATAAATTTAGTGTTGATGCTTATAATGTATATGTTAAAGGAATGACA
TTAAATGTTTTAGATATGGTAGCAATATGGCCTTCATTATATCCAAATGATTATACTTCACAAACAACCTTAGAA
CAAACACGTGTCACTTTTTCAAATATGGTTGGTCAAGAAGAAGGTACAGATGGAACCCTAAAAATTTACAATACT
TTTGATTCTAGTAGTTTTCAACATAGCCTAATACCTAATAATAATGTTGATTTAATTTCTTATTTTAATGATGAA
TTGCAAAATTTAGAATTAGCAGTATATACCCCTCCTAAAAAGGATAGTGGATATAGTTATCCTTATGGATTTGTT
TTAAAATATGCAAACAGTAAATATAAATATGGTGATAGCAATGATCCAGAATCTTTAGGAGGATTATCCACACTA
TCTGCACCTATACAACAAATAAATGCAGCAACTCAAAACAGTAAATATCTAGATGGAGAAACAATAAATGGAATA
GGGGCGTCCTTACCTGGTTATTGTACTACAGGATGTTCAGCAACAGAACAACCTTTTAGTTGTACTTCTAATGCT
AATAGCTATAAATCAAGCTGTAATCCTTCAGATACTAATCAAAAAATTAATGCTTTATATGCTTTTACACAAACT
AATGTAAAGGGAAACACGGGAAATTAGGAGTACTGGCAAGTCTTGTTCCATATGATTTAAATCCTAAAAATGTA
TTTGGTGAATTAGATTCAGATACAAATAATGTTATCTTAAAAGGAATTCCTGCAGAAAAAGGGTATTTTTCTAAT
AATGCGCGACCTACTGTTGTAAAAGAATGGATTAATGGTGCAAGTGCTGTACCACTTTATTCAGGAAATACTTTA
TTTATGACGGCTACGAATTTAACAGCTACTCAATATAAAATTAGAATACGTTATGCAAATCCAAATTCAGATACT
CAAATCGGTGTACGAATTACGCAAAATGGTTCTCTAATTTCCAATAGTAATCCACCGCTTTATAGTACTACTGAT
TCAAGTATGAGTAGTAATTTACCACAAAATGTATATGTCACAGGGGAAAATGGAAATTATACACTTCTAGATTTA
TATAGTACTAATAATGTTTTATCAACAGGAGATATTACATTACAACTTACAGGAGGAAATCAAAAAATATTTATT
GATCGAATAGAATTTATACCTACTATGCCTGTACCTGCTGCTACTAACAACAATAACGGCGATAACGATCCCCCA
CCGATACACCACGGTTGTGCAATAGCTGGTACACAACAACTTTGTGCTGGACCACCTAAGTTTGAACAAGTAAGT
GATTTAGAAAAAATTACAACGCAAGTATATATGTTATTCAAATCTTCTTTGTATGAAGAATTAGATCCAAAAGTT
TCCAGCTATCAAATTAATCAAGTAGCATTGAAAGTTATGGCACTATCTAATGAAAAGTTTTGTGAAGAAAAAAGA
TTGTTACGAAAATTAGTCAATAAAGCAAACCAATTACTAGAAGCACGTAACTTACTAGTAGGTGGAAATTTTGAA
ACAACTCAAAATTGGGTACTTGGAACAAATGCTTATATAAATTATGATTCGTTTTTATTTAATGGAAATTATTTA
TCCTTACAACCAGCAAGTGGATTTTTCACATCTTATGCTTATCAAAAAATAGATGAGTCAACATTAAAACCCTAT
ACACGATATAAAGTTTCTGGATTCATTGGGCAAAGTAATCAAGTAGAACTTATTATTTCTCGTTATGGAAAAGAA
ATTGATAAAATATTAAATGTTCCATATGCAGGGCCTCTTCCTATTACTGCTGATGCATCGATAACTTGTTGTGCA
CCAGAAATAGACCAATGTGATGGGGGCAATCTGATTCTCATTTCTTCAACTATAGCATCGATGTAGGTGCACTT
CACCCAGAATTAAACCCTGGCATTGAAATTGGTCTTAAAATTGTGCAATCAAATGGTAATATAACAATTAGTAAT
CTAGAAATTATTGAAGAACGTCCACTTACAGAAATGGAAATTCAAACAGTCAATCGAAAAGATCAAAAATGGAAA
AGAGAAAAACTTCTAGAATGTGCAAGTATTAGTGAACTTTTACAACCAATCATTAATCAAATCGATTCATTGTTC
AAAGATGCAAACTGGTATAATGATATTCTTCCTCATGTCACATATCAAACTCTAAAAAATATTATAGTACCCGAT
TTACCAAAATTAAAACATTGGTTCATAGATGATCTCCCAGGTGAATATTATGAAATTGAACAAAAAATGAAAGAA
GCTCTAAAACATGCATTTACACAATTAGACGAGAAAATTTAATCTACAATGGTGACTTTACAACTAACTTAATA
GATTGGCAAATAGAAGGTGATGCTCGAATGAAAGTATTAGAAAATAATGCTTTGGCATTACAACTTTCCAATTGG
GATTCTAGTGTTTCACAATCTATTGATATATTAGAATTTGATGAAGATAAAGCATATAAACTTCGCGTATATGCT
CAAGGAAGCGGAACAATCCAATTTGGAAACTGTGAAGATGAAGCCATCCAATTTAATACAAACTCATTCGTATAT
AAAGAAAAAATAATATATTTCGATACCCCATCAATTAACTTACACATACAATCAGAAGGTCCTGAATTCGTTGTA
AGTAGTATCGACCTCGTTGAATTATCAGACGACGAATAA (SEQ ID NO:2)
```

Figure 2a

MRMDCNLQSQQNIPYNVLAIPVSNVNALVDTAKDLKEAWEAFQKTGSFSLTALQQGFSASQGGAF
NYLTLLQSGISLAGSFVPGGTFVAPIVNMVIGWLWPHKNKTADTENLIKLIDEEIQKQLNKALLE
QDKNNWTSFLESIFDVSNTVSNAMIDAQWSGTVDTTNRQPKTPTTSDYLNVVGKFDSADSAIVTN
ENQIMNGNFDVAASPYFVIGATLRLSLFQSYIKFCNNWIDAVGFNPSDSNTQKANLARMKQTMRI
TINEYTQRIMKVFKDPKNMPTIGTNKFSVDAYNVYVKGMTLNVLDMVAIWPSLYPNDYTSQTTLE
QTRVTFSNMVGQEEGTDGTLKIYNTFDSSSFQHSLIPNNNVDLISYFNDELQNLELAVYTPPKKD
SGYSYPYGFVLKYANSKYKYGDSNDPESLGGLSTLSAPIQQINAATQNSKYLDGETINGIGASLP
GYCTTGCSATEQPFSCTSNANSYKSSCNPSDTNQKINALYAFTQTNVKGNTGKLGVLASLVPYDL
NPKNVFGELDSDTNNVILKGIPAEKGYFSNNARPTVVKEWINGASAVPLYSGNTLFMTATNLTAT
QYKIRIRYANPNSDTQIGVRITQNGSLISNSNPPLYSTTDSSMSSNLPQNVYVTGENGNYTLLDL
YSTNNVLSTGDITLQLTGGNQKIFIDRIEFIPTM (SEQ ID NO:3)

Figure 2b

ATGCGAATGGATTGTAATTTACAATCACAACAAAATATTCCTTATAATGTATTAGCAATACCAGT
ATCTAATGTTAATGCGTTGGTTGATACAGCTAAAGATTTAAAAGAAGCATGGGAAGCATTTCAAA
AAACTGGTTCTTTTTCATTAACAGCTTTACAACAAGGATTTTCTGCCTCACAAGGAGGAGCATTC
AATTATTTAACATTATTACAATCAGGAATATCATTAGCTGGTTCTTTTGTCCCTGGAGGTACTTT
TGTAGCACCCATTGTTAATATGGTTATTGGTTGGTTATGGCCACATAAAAACAAGACAGCGGATA
CAGAAAATTTAATAAAATTAATTGATGAAGAAATTCAAAAACAATTAAACAAAGCCTTATTAGAG
CAAGATAAAAACAATTGGACCTCTTTTTTAGAAAGTATATTTGATGTTTCAAATACAGTAAGTAA
TGCAATGATAGATGCTCAGTGGTCAGGTACTGTAGATACTACAAATAGACAACCAAAAACTCCAA
CAACATCAGATTATCTAAATGTTGTTGGAAAATTTGATTCAGCGGATTCTGCAATTGTAACTAAT
GAAAATCAAATAATGAACGGCAACTTTGACGTAGCTGCATCACCCTATTTTGTTATAGGAGCAAC
ATTACGTCTTTCATTATTTCAATCTTATATTAAATTTTGTAATAATTGGATTGATGCAGTTGGAT
TTAATCCATCAGATTCTAATACACAAAAGGCTAATTTAGCTCGTATGAAACAAACTATGCGTATT
ACAATTAACGAGTATACACAAGAATTATGAAAGTTTTTAAAGATCCCAAGAATATGCCTACAAT
AGGTACTAATAAATTTAGTGTTGATGCTTATAATGTATATGTTAAAGGAATGACATTAAATGTTT
TAGATATGGTAGCAATATGGCCTTCATTATATCCAAATGATTATACTTCACAAACAACCTTAGAA
CAAACACGTGTCACTTTTTCAAATATGGTTGGTCAAGAAGAAGGTACAGATGGAACCCTAAAAAT
TTACAATACTTTTGATTCTAGTAGTTTTCAACATAGCCTAATACCTAATAATAATGTTGATTTAA
TTTCTTATTTTAATGATGAATTGCAAAATTTAGAATTAGCAGTATATACCCCTCCTAAAAAGGAT
AGTGGATATAGTTATCCTTATGGATTTGTTTTAAAATATGCAAACAGTAAATATAAATATGGTGA
TAGCAATGATCCAGAATCTTTAGGAGGATTATCCACACTATCTGCACCTATACAACAAATAAATG
CAGCAACTCAAAACAGTAAATATCTAGATGGAGAAACAATAAATGGAATAGGGCGTCCTTACCT
GGTTATTGTACTACAGGATGTTCAGCAACAGAACAACCTTTTAGTTGTACTTCTAATGCTAATAG
CTATAAATCAAGCTGTAATCCTTCAGATACTAATCAAAAAATTAATGCTTTATATGCTTTTACAC
AAACTAATGTAAAGGGAAACACGGGGAAATTAGGAGTACTGGCAAGTCTTGTTCCATATGATTTA
AATCCTAAAAATGTATTTGGTGAATTAGATTCAGATACAAATAATGTTATCTTAAAAGGAATTCC
TGCAGAAAAGGGTATTTTTCTAATAATGCGCGACCTACTGTTGTAAAAGAATGGATTAATGGTG
CAAGTGCTGTACCACTTTATTCAGGAAATACTTTATTTATGACGGCTACGAATTTAACAGCTACT
CAATATAAAATTAGAATACGTTATGCAAATCCAAATTCAGATACTCAAATCGGTGTACGAATTAC
GCAAAATGGTTCTCTAATTTCCAATAGTAATCCACCGCTTTATAGTACTACTGATTCAAGTATGA
GTAGTAATTTACCACAAAATGTATATGTCACAGGGGAAAATGGAAATTATACACTTCTAGATTTA
TATAGTACTAATAATGTTTTATCAACAGGAGATATTACATTACAACTTACAGGAGGAAATCAAAA
AATATTTATTGATCGAATAGAATTTATACCTACTATG (SEQ ID NO:4)

Figure 3a

MANKHLSLSLFLVLLGLSASLASGRMDCNLQSQQNIPYNVLAIPVSNVNALVDTAKDLKEAWEAF
QKTGSFSLTALQQGFSASQGGAFNYLTLLQSGISLAGSFVPGGTFVAPIVNMVIGWLWPHKNKTA
DTENLIKLIDEEIQKQLNKALLEQDKNNWTSFLESIFDVSNTVSNAMIDAQWSGTVDTTNRQPKT
PTTSDYLNVVGKFDSADSAIVTNENQIMNGNFDVAASPYFVIGATLRLSLFQSYIKFCNNWIDAV
GFNPSDSNTQKANLARMKQTMRITINEYTQRIMKVFKDPKNMPTIGTNKFSVDAYNVYVKGMTLN
VLDMVAIWPSLYPNDYTSQTTLEQTRVTFSNMVGQEEGTDGTLKIYNTFDSSSFQHSLIPNNNVD
LISYFNDELQNLELAVYTPPKKDSGYSYPYGFVLKYANSKYKYGDSNDPESLGGLSTLSAPIQQI
NAATQNSKYLDGETINGIGASLPGYCTTGCSATEQPFSCTSNANSYKSSCNPSDTNQKINALYAF
TQTNVKGNTGKLGVLASLVPYDLNPKNVFGELDSDTNNVILKGIPAEKGYFSNNARPTVVKEWIN
GASAVPLYSGNTLFMTATNLTATQYKIRIRYANPNSDTQIGVRITQNGSLISNSNPPLYSTTDSS
MSSNLPQNVYVTGENGNYTLLDLYSTNNVLSTGDITLQLTGGNQKIFIDRIEFIPTM (SEQ ID
NO:5)

Figure 3b

ATGGCCAACAAGCACCTGTCCCTCTCCCTCTTCCTCGTGCTCCTCGGCCTCTCCGCCTCCCTCGC
CTCCGGAAGGATGGATTGCAACCTTCAGTCTCAGCAGAACATTCCTTACAACGTGCTGGCCATTC
CCGTGTCCAACGTGAACGCTCTGGTCGACACTGCTAAGGACCTCAAGGAGGCTTGGGAGGCCTTC
CAGAAGACCGGGTCCTTCTCTCTCACAGCCTTGCAGCAGGGATTCTCTGCATCTCAGGGAGGAGC
CTTCAACTACCTCACCTTGCTTCAGTCCGGCATCTCCTTGGCAGGCTCCTTCGTCCCAGGAGGAA
CCTTCGTCGCACCTATCGTCAACATGGTGATTGGATGGCTGTGGCCTCACAAGAACAAGACCGCC
GACACCGAGAACCTCATCAAACTGATCGACGAGGAGATCCAGAAGCAGCTGAACAAGGCTTTGCT
GGAGCAGGACAAGAACAACTGGACTTCCTTCCTCGAGTCCATCTTCGACGTCTCCAACACCGTGT
CCAACGCCATGATCGACGCTCAGTGGTCTGGCACTGTGGACACTACCAACAGGCAGCCTAAGACT
CCCACTACTTCCGACTATCTCAACGTCGTGGGAAAGTTCGACTCCGCAGACTCTGCCATTGTGAC
CAACGAGAACCAGATCATGAACGGCAACTTCGACGTGGCTGCCTCTCCTTACTTCGTGATCGGAG
CTACCCTCAGATTGTCCCTCTTCCAGTCCTACATCAAGTTCTGCAACAACTGGATCGATGCTGTG
GGCTTCAACCCTTCCGACTCTAACACCCAGAAGGCCAACCTTGCCAGGATGAAGCAGACCATGAG
GATCACCATCAACGAGTACACTCAGCGCATCATGAAGGTGTTCAAGGACCCCAAGAACATGCCCA
CTATCGGGACCAACAAGTTCTCCGTTGACGCCTACAACGTCTACGTGAAAGGGATGACCCTCAAC
GTGCTCGACATGGTGGCTATCTGGCCATCTCTCTATCCCAACGACTACACTTCTCAGACCACTCT
TGAGCAGACTCGCGTGACCTTCTCCAACATGGTCGGACAGGAAGAGGGTACTGACGGGACTCTCA
AGATCTACAACACCTTCGACTCCTCTTCCTTCCAGCACTCCCTCATTCCCAACAACAACGTGGAC
TTGATCTCCTACTTCAACGACGAGCTCCAGAACCTCGAGCTCGCTGTGTACACTCCTCCCAAGAA
GGACTCCGGTTACTCCTACCCTTACGGCTTCGTGCTCAAGTACGCCAACTCTAAGTACAAGTACG
GCGACTCCAACGACCCTGAGTCCTTGGGAGGACTCTCCACACTGTCCGCACCTATCCAGCAGATC
AACGCTGCTACCCAGAACTCCAAGTACCTCGACGGTGAGACCATCAACGGCATCGGAGCTTCCCT
TCCAGGCTACTGCACTACCGGATGCTCAGCTACCGAGCAGCCTTTCAGTTGCACCTCCAACGCCA
ACTCCTACAAGTCCTCCTGCAACCCTTCCGACACCAACCAGAAGATCAACGCTCTCTACGCCTTC
ACTCAGACCAACGTGAAGGGTAACACTGGCAAGCTCGGAGTGCTCGCTTCACTGGTGCCCTACGA
CCTCAACCCTAAGAACGTGTTCGGAGAGTTGGACTCCGACACCAACAACGTGATTCTCAAGGGTA
TCCCTGCCGAGAAGGGCTACTTCTCCAACAACGCTCGCCCTACCGTCGTCAAGGAGTGGATCAAC
GGAGCTTCTGCCGTGCCACTGTACTCTGGCAACACCCTGTTCATGACCGCTACCAACCTCACCGC
TACCCAGTACAAGATCCGCATACGCTACGCCAACCCCAACTCTGACACTCAGATCGGCGTCAGGA
TCACCCAGAACGGCTCTCTGATCTCCAACTCCAACCCTCCCTTGTACTCCACCACTGACTCCTCC
ATGTCCTCCAACCTTCCTCAGAACGTGTACGTGACCGGCGAGAACGGGAACTACACTCTTCTGGA
CCTGTACTCTACCAACAACGTCCTGTCCACTGGAGACATCACTCTGCAGCTGACAGGTGGGAACC
AGAAGATCTTCATCGACCGCATTGAGTTCATTCCCACCATGTAG (SEQ ID NO:6)

ENDOTOXINS HAVING NEMATOCIDAL ACTIVITY AND METHODS OF USE THEREOF

CROSS-REFERENCE TO RELATED APPLICATIONS

This application claims the benefit of U.S. Provisional Application 61/489,463, filed May 24, 2011, herein incorporated by reference in its entirety.

FIELD OF THE INVENTION

The present invention relates to polypeptides having pesticidal, particularly nematicidal, activity and polynucleotides that encode the same. Methods of the invention utilize these pesticidal polynucleotides and polypeptides to control plant pests and to increase pest resistance in plants.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 414532SEQLIST.TXT, created on May 23, 2012, and having a size of 31 kilobytes, and is filed concurrently with the specification. The sequence listing contained in this ASCII formatted document is part of the specification and is herein incorporated by reference in its entirety.

BACKGROUND OF THE INVENTION

Plant pests, including plant-parasitic nematodes, are a major factor in the loss of the world's agricultural crops. Agriculturally significant nematodes include the sedentary endoparasites, such as those found in the genera *Meloidogyne* (root-knot nematodes), *Heterodera*, and *Globedera* (cyst nematodes).

Currently, plant-parasitic nematodes are generally controlled by chemical nematicides, crop rotation, and growing resistant cultivars. The use of chemical nematicides, however, increases costs to farmers and can cause harmful effects on the ecosystem. Moreover, consumers and government regulators alike are becoming increasingly concerned with the environmental hazards associated with the production and use of synthetic agrochemicals. Traditional breeding methods can be used to select resistant cultivars, but the methods are time-consuming and require continuous effort to maintain disease resistance. See, for example, Grover and Gowthaman (2003) *Curr. Sci.* 84:330-340. Thus, there is substantial interest in developing novel alternatives for the control of plant pathogens that possess a lower risk of pollution and environmental hazards than is characteristic of traditional agrochemical-based methods and that are less cumbersome than conventional breeding techniques.

A number of biotechnology-based strategies, including disruption of the feeding structure of the nematodes by localized expression of phytotoxic gene product(s) have been investigated, but none of them have reached commercial success. Nevertheless, biological control of plant pests of agricultural significance using a microbial agent, such as proteins derived from fungi, bacteria, or insects, affords an environmentally friendly and commercially attractive alternative to synthetic chemical pesticides. Generally speaking, the use of biopesticides presents a lower risk of pollution and environmental hazards, and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus*, notably *Bacillus thuringiensis* and *Bacillus papilliae*, are known to possess pesticidal activity against a broad range of pests, including insects and nematodes. Pesticidal activity appears to be concentrated in parasporal crystalline protein inclusions, although pesticidal proteins have also been isolated from the vegetative growth stage of *Bacillus*. Agricultural scientists have developed crop plants with enhanced insect resistance by genetically engineering the plants to produce pesticidal proteins from *Bacillus*. For example, corn and cotton plants have been genetically engineered to produce pesticidal proteins isolated from strains of *B. thuringiensis* known as δ-endotoxins or Cry toxins (see, e.g., Aronson (2002) *Cell Mol. Life. Sci.* 59(3):417-425; Schnepf et al. (1998) *Microbiol Mol Biol Rev.* 62(3):775-806). These genetically engineered crops are now widely used in American agriculture and have provided the farmer with an environmentally friendly alternative to traditional insect-control methods. Similarly, potatoes genetically engineered to contain pesticidal Cry toxins have been sold to the American farmer.

There remains a need for biopesticides, such as Bt toxins, having nematicidal activity and methods of using such biopesticides to protect crops from plant-parasitic nematodes.

BRIEF SUMMARY OF THE INVENTION

Compositions and methods for protecting a plant from a pest are provided. The compositions comprise δ-endotoxin polypeptides that display pesticidal activity against nematodes, including plant-parasitic nematodes. Polynucleotides comprising nucleotide sequences that encode the presently disclosed δ-endotoxin polypeptides are further provided. Compositions also include expression cassettes comprising a polynucleotide that encodes a δ-endotoxin polypeptide disclosed herein. Plants, plant cells, seeds, and microorganisms comprising the presently disclosed polynucleotides and polypeptides are further provided.

The compositions are useful in methods directed to inducing pest resistance, particularly plant-parasitic nematode resistance in plants. In particular embodiments, the methods comprise introducing into a plant at least one polynucleotide that encodes a pesticidal (e.g., nematicidal) δ-endotoxin polypeptide. As a result, the pesticidal δ-endotoxin polypeptide is expressed in the plant, and the pest (e.g., plant parasitic nematode) is exposed to the preferred protein at the site of attack, thereby leading to increased pest resistance. A tissue-preferred promoter may be used to drive expression of a pesticidal δ-endotoxin protein in specific plant tissues that are particularly vulnerable to pest attack. For control of nematodes, a root preferred promoter may be used.

Further provided are biopesticide compositions and formulations and methods for their use in protecting a plant from a pest, particularly a plant-parasitic nematode. In some embodiments, the compositions comprise a carrier in combination with a pesticidal (e.g., nematicidal) δ-endotoxin polypeptide or a microorganism comprising a polynucleotide that encodes a pesticidal (e.g., nematicidal) δ-endotoxin polypeptide. Methods of using these compositions to protect a plant from a pest comprise applying the biopesticide composition to the environment of a plant pest by, for example, spraying, dusting, broadcasting, or seed coating.

The following embodiments are encompassed by the present invention:

1. An isolated polypeptide comprising an amino acid sequence selected from the group consisting of:
   (a) the amino acid sequence set forth in SEQ ID NO: 1;
   (b) an amino acid sequence having at least 93% sequence identity to SEQ ID NO: 1, wherein said polypeptide has nematicidal activity;
   (c) an amino acid sequence comprising at least 178 consecutive amino acids of SEQ ID NO: 1, wherein said polypeptide has nematicidal activity;
   (d) an amino acid sequence having at least 91% sequence identity to residues 23-684 of SEQ ID NO: 1, wherein said polypeptide has nematicidal activity; and
   (e) an amino acid sequence comprising at least 89 consecutive amino acids from residues 23-684 of SEQ ID NO: 1, wherein said polypeptide has nematicidal activity.

2. An isolated polypeptide that binds to a glycolipid comprising the tetrasaccharide sequence N-acetylgalactosamine β1-4 N-acetylglucosamine β1-3 mannose β1-4 glucose and facilitates the formation of a pore in an invertebrate cellular membrane containing said glycolipid, wherein said polypeptide comprises an amino acid sequence selected from the group consisting of:
   (a) an amino acid sequence having at least 93% sequence identity to SEQ ID NO: 1;
   (b) an amino acid sequence comprising at least 178 consecutive amino acids of SEQ ID NO: 1;
   (c) an amino acid sequence having at least 91% sequence identity to residues 23-684 of SEQ ID NO: 1; and
   (d) an amino acid sequence comprising at least 89 consecutive amino acids from residues 23-684 of SEQ ID NO: 1;
   wherein said polypeptide has pesticidal activity.

3. The isolated polypeptide of embodiment 2, wherein said polypeptide has nematicidal activity.

4. The isolated polypeptide of embodiment 1 or 3, wherein said polypeptide has nematicidal activity against a nematode that is a member of a *Meloidogyne, Heterodera*, or *Globedera* genera, or a nematode selected from the group consisting of *Panagrellus redivivus, Distolabrellus veechi, Nippostrongylus brasiliensis*, and *Caenorhabditis elegans*.

5. An isolated polynucleotide comprising a nucleotide sequence selected from the group consisting of:
   (a) the nucleotide sequence set forth in SEQ ID NO: 2;
   (b) a nucleotide sequence encoding an amino acid sequence comprising SEQ ID NO: 1;
   (c) a nucleotide sequence having at least 90% sequence identity to SEQ ID NO: 2, wherein said polynucleotide encodes a polypeptide having nematicidal activity;
   (d) a nucleotide sequence encoding an amino acid sequence having at least 93% sequence identity to SEQ ID NO: 1, wherein said polynucleotide encodes a polypeptide having nematicidal activity;
   (e) a nucleotide sequence encoding an amino acid sequence comprising at least 178 consecutive amino acids of SEQ ID NO: 1, wherein said polypeptide has nematicidal activity;
   (f) a nucleotide sequence encoding an amino acid sequence having at least 91% sequence identity to residues 23-684 of SEQ ID NO: 1, wherein said polypeptide has nematicidal activity; and
   (g) a nucleotide sequence encoding an amino acid sequence comprising at least 89 consecutive amino acids from residues 23-684 of SEQ ID NO: 1, wherein said polypeptide has nematicidal activity.

6. An isolated polynucleotide comprising a nucleotide sequence encoding a polypeptide that binds to a glycolipid comprising the tetrasaccharide sequence N-acetylgalactosamine β1-4 N-acetylglucosamine β1-3 mannose β1-4 glucose and facilitates the formation of a pore in an invertebrate cellular membrane containing said glycolipid, wherein said polynucleotide comprises a nucleotide sequence selected from the group consisting of:
   (a) a nucleotide sequence having at least 90% sequence identity to SEQ ID NO: 2;
   (b) a nucleotide sequence encoding an amino acid sequence having at least 93% sequence identity to SEQ ID NO: 1;
   (c) a nucleotide sequence encoding an amino acid sequence comprising at least 178 consecutive amino acids of SEQ ID NO: 1;
   (d) a nucleotide sequence encoding an amino acid sequence having at least 91% sequence identity to residues 23-684 of SEQ ID NO: 1; and
   (e) a nucleotide sequence encoding an amino acid sequence comprising at least 89 consecutive amino acids from residues 23-684 of SEQ ID NO: 1;
   wherein said polypeptide has pesticidal activity.

7. The isolated polynucleotide of embodiment 6, wherein said polynucleotide encodes a polypeptide having nematicidal activity.

8. The isolated polynucleotide of embodiment 5 or 7, wherein said polynucleotide encodes a polypeptide having nematicidal activity against a nematode that is a member of a *Meloidogyne, Heterodera*, or *Globedera* genera, or a nematode selected from the group consisting of *Panagrellus redivivus, Distolabrellus veechi, Nippostrongylus brasiliensis*, and *Caenorhabditis elegans*.

9. An expression cassette comprising the polynucleotide of embodiment 5 or 6.

10. The expression cassette of embodiment 9, wherein said polynucleotide is operably linked to a promoter that drives expression in a plant.

11. The expression cassette of embodiment 9, wherein said polynucleotide is operably linked to a promoter that drives expression in a microorganism.

12. A host cell comprising the polynucleotide of embodiment 5 or 6.

13. A host cell comprising the expression cassette of embodiment 9.

14. A plant comprising a heterologous polynucleotide operably linked to a promoter that drives expression in the plant, wherein said heterologous polynucleotide comprises a nucleotide sequence selected from the group consisting of:
   (a) the nucleotide sequence set forth in SEQ ID NO: 2;
   (b) a nucleotide sequence encoding the amino acid sequence comprising SEQ ID NO: 1;
   (c) a nucleotide sequence having at least 90% sequence identity to SEQ ID NO: 2, wherein said polynucleotide encodes a polypeptide having nematicidal activity;
   (d) a nucleotide sequence encoding an amino acid sequence having at least 93% sequence identity to SEQ ID NO: 1, wherein said polynucleotide encodes a polypeptide having nematicidal activity;
   (e) a nucleotide sequence encoding an amino acid sequence comprising at least 178 consecutive amino acids of SEQ ID NO: 1, wherein said polypeptide has nematicidal activity;
   (f) a nucleotide sequence encoding an amino acid sequence having at least 91% sequence identity to residues 23-684 of SEQ ID NO: 1, wherein said polypeptide has nematicidal activity; and
   (g) a nucleotide sequence encoding an amino acid sequence comprising at least 89 consecutive amino acids from residues 23-684 of SEQ ID NO: 1, wherein said polypeptide has nematicidal activity.

15. The plant of embodiment 14, wherein said heterologous polynucleotide encodes a polypeptide having nematicidal activity against a nematode that is a member of a *Meloidogyne, Heterodera*, or *Globedera* genera, or a nematode selected from the group consisting of *Panagrellus redivivus, Distolabrellus veechi, Nippostrongylus brasiliensis*, and *Caenorhabditis elegans*.

16. The plant of embodiment 14, wherein said promoter is a root-preferred promoter.

17. The plant of embodiment 14, wherein said plant is a monocot.

18. The plant of embodiment 17, wherein said monocot is maize, sugarcane, wheat, rice, barley, sorghum, or rye.

19. The plant of embodiment 14, wherein said plant is a dicot.

20. The plant of embodiment 19, wherein said dicot is soybean, *Brassica*, sunflower, cotton, alfalfa, or tomato.

21. A transformed seed of the plant of any one of embodiments 14-20.

22. A method of enhancing pest resistance in a plant, said method comprising providing to said plant a polypeptide selected from the group consisting of:
 (a) the amino acid sequence set forth in SEQ ID NO: 1;
 (b) an amino acid sequence having at least 93% sequence identity to SEQ ID NO: 1, wherein said polypeptide has nematicidal activity;
 (c) an amino acid sequence comprising at least 178 consecutive amino acids of SEQ ID NO: 1, wherein said polypeptide has nematicidal activity;
 (d) an amino acid sequence having at least 91% sequence identity to residues 23-684 of SEQ ID NO: 1, wherein said polypeptide has nematicidal activity; and
 (e) an amino acid sequence comprising at least 89 consecutive amino acids from residues 23-684 of SEQ ID NO: 1, wherein said polypeptide has nematicidal activity.

23. The method of embodiment 22, wherein said polypeptide has nematicidal activity against a nematode that is a member of a *Meloidogyne, Heterodera*, or *Globedera* genera, or a nematode selected from the group consisting of *Panagrellus redivivus, Distolabrellus veechi, Nippostrongylus brasiliensis*, and *Caenorhabditis elegans*.

24. The method of embodiment 22, wherein said plant is planted in an area of cultivation, wherein said area of cultivation comprises said pest, or wherein environmental conditions in said area of cultivation are conducive to the growth of said pest.

25. The method of embodiment 22, wherein providing the polypeptide comprises introducing into said plant a heterologous polynucleotide comprising a nucleotide sequence selected from the group consisting of:
 (a) the nucleotide sequence set forth in SEQ ID NO: 2;
 (b) a nucleotide sequence encoding the amino acid sequence comprising SEQ ID NO: 1;
 (c) a nucleotide sequence having at least 90% sequence identity to SEQ ID NO: 2, wherein said polynucleotide encodes a polypeptide having nematicidal activity;
 (d) a nucleotide sequence encoding an amino acid sequence having at least 93% sequence identity to SEQ ID NO: 1, wherein said polynucleotide encodes a polypeptide having nematicidal activity;
 (e) a nucleotide sequence encoding an amino acid sequence comprising at least 178 consecutive amino acids of SEQ ID NO: 1, wherein said polypeptide has nematicidal activity;
 (f) a nucleotide sequence encoding an amino acid sequence having at least 91% sequence identity to residues 23-684 of SEQ ID NO: 1, wherein said polypeptide has nematicidal activity; and
 (g) a nucleotide sequence encoding an amino acid sequence comprising at least 89 consecutive amino acids from residues 23-684 of SEQ ID NO: 1, wherein said polypeptide has nematicidal activity.

26. The method of embodiment 25, wherein said heterologous polynucleotide encodes a polypeptide having nematicidal activity against a nematode that is a member of a *Meloidogyne, Heterodera*, or *Globedera* genera, or a nematode selected from the group consisting of *Panagrellus redivivus, Distolabrellus veechi, Nippostrongylus brasiliensis*, and *Caenorhabditis elegans*.

27. The method of embodiment 25, wherein said heterologous polynucleotide is stably integrated into the genome of the plant.

28. The method of embodiment 25, wherein said heterologous polynucleotide is operably linked to a promoter active in said plant.

29. The method of embodiment 28, wherein said promoter is a tissue-preferred promoter.

30. The method of embodiment 29, wherein said tissue-preferred promoter is a root-preferred promoter.

31. A biopesticide composition comprising at least one polypeptide according to embodiment 1 or 2.

32. The biopesticide composition of embodiment 31 further comprising a carrier.

33. A method for protecting a plant from a plant pest comprising applying the composition according to embodiment 31 to the environment of a plant pest.

34. The method of embodiment 33, wherein said composition is applied by a procedure selected from the group consisting of spraying, dusting, broadcasting, and seed coating.

35. The method of embodiment 33, wherein said plant pest is a nematode.

36. The method of embodiment 35, wherein said nematode is a member of a *Meloidogyne, Heterodera*, or *Globedera* genera.

37. A microorganism comprising at least one heterologous polynucleotide operably linked to a promoter that drives expression in the microorganism, wherein said heterologous polynucleotide comprises a nucleotide sequence selected from the group consisting of:
 (a) the nucleotide sequence set forth in SEQ ID NO: 2;
 (b) a nucleotide sequence encoding the amino acid sequence comprising SEQ ID NO: 1;
 (c) a nucleotide sequence having at least 90% sequence identity to SEQ ID NO: 2, wherein said polynucleotide encodes a polypeptide having nematicidal activity;
 (d) a nucleotide sequence encoding an amino acid sequence having at least 93% sequence identity to SEQ ID NO: 1, wherein said polynucleotide encodes a polypeptide having nematicidal activity;
 (e) a nucleotide sequence encoding an amino acid sequence comprising at least 178 consecutive amino acids of SEQ ID NO: 1, wherein said polypeptide has nematicidal activity;
 (f) a nucleotide sequence encoding an amino acid sequence having at least 91% sequence identity to residues 23-684 of SEQ ID NO: 1, wherein said polypeptide has nematicidal activity; and
 (g) a nucleotide sequence encoding an amino acid sequence comprising at least 89 consecutive amino acids from residues 23-684 of SEQ ID NO: 1, wherein said polypeptide has nematicidal activity.

38. The microorganism of embodiment 37, wherein said heterologous polynucleotide encodes a polypeptide having nematicidal activity against a nematode that is a member of a *Meloidogyne, Heterodera*, or *Globedera* genera, or a nematode selected from the group consisting of *Panagrellus redivivus, Distolabrellus veechi, Nippostrongylus brasiliensis*, and *Caenorhabditis elegans*.

39. A biopesticide composition comprising at least one microorganism according to embodiment 37.

40. The biopesticide composition of embodiment 39 further comprising a carrier.

41. A method for protecting a plant from a pest comprising applying the biopesticide composition according to embodiment 39 to the environment of a plant pest.

42. The method of embodiment 41, wherein said biopesticide composition is applied by a procedure selected from the group consisting of spraying, dusting, broadcasting, and seed coating.

43. The method of embodiment 41, wherein said plant pest is a nematode.

44. The method of embodiment 43, wherein said nematode is a member of a *Meloidogyne, Heterodera*, or *Globedera* genera.

45. A method for controlling a pest in an area of cultivation, said method comprising:
   a) evaluating environmental conditions in an area of cultivation for the presence of a pest or conditions conducive to the growth of a pest;
   b) selecting an effective amount of a biopesticide composition, wherein the biopesticide composition is the biopesticide composition according to embodiment 31 or embodiment 40; and
   c) applying said biopesticide composition to a crop, crop part, seed, or an area of cultivation of said crop.

46. A method for controlling a pest in an area of cultivation, said method comprising:
   a) evaluating environmental conditions in an area of cultivation for the presence of a pest or conditions conducive to the growth of a pest; and
   b) planting the area with crop seeds or plants comprising a heterologous polynucleotide operably linked to a promoter that drives expression in the plant, wherein said heterologous polynucleotide comprises a nucleotide sequence selected from the group consisting of:
      (i) the nucleotide sequence set forth in SEQ ID NO: 2;
      (ii) a nucleotide sequence encoding the amino acid sequence comprising SEQ ID NO: 1;
      (iii) a nucleotide sequence having at least 90% sequence identity to SEQ ID NO: 2, wherein said polynucleotide encodes a polypeptide having nematicidal activity;
      (iv) a nucleotide sequence encoding an amino acid sequence having at least 93% sequence identity to SEQ ID NO: 1, wherein said polynucleotide encodes a polypeptide having nematicidal activity;
      (v) a nucleotide sequence encoding an amino acid sequence having at least 91% sequence identity to residues 23-684 of SEQ ID NO: 1, wherein said polypeptide has nematicidal activity; and
      (vi) a nucleotide sequence encoding an amino acid sequence comprising at least 89 consecutive amino acids from residues 23-684 of SEQ ID NO: 1, wherein said polypeptide has nematicidal activity.

47. The method of embodiment 45 or 46, wherein said pest is a nematode.

48. The method of embodiment 47, wherein said nematode is a member of a *Meloidogyne, Heterodera*, or *Globedera* genera.

These and other aspects of the invention are disclosed in more detail in the description of the invention given below.

BRIEF DESCRIPTION OF THE FIGURES

FIG. 1 depicts the amino acid and nucleic acid coding sequences for RX008, a novel *Bacillus thuringiensis* crystal protein isolated from strain MG3G12.

FIG. 2 depicts the amino acid and nucleic acid coding sequences for an active C-terminal truncation variant of RX008.

FIG. 3 depicts the amino acid and nucleic acid coding sequences for an RX008 variant that has been optimized for expression in soybean plants.

DETAILED DESCRIPTION OF THE INVENTION

Figure 4:
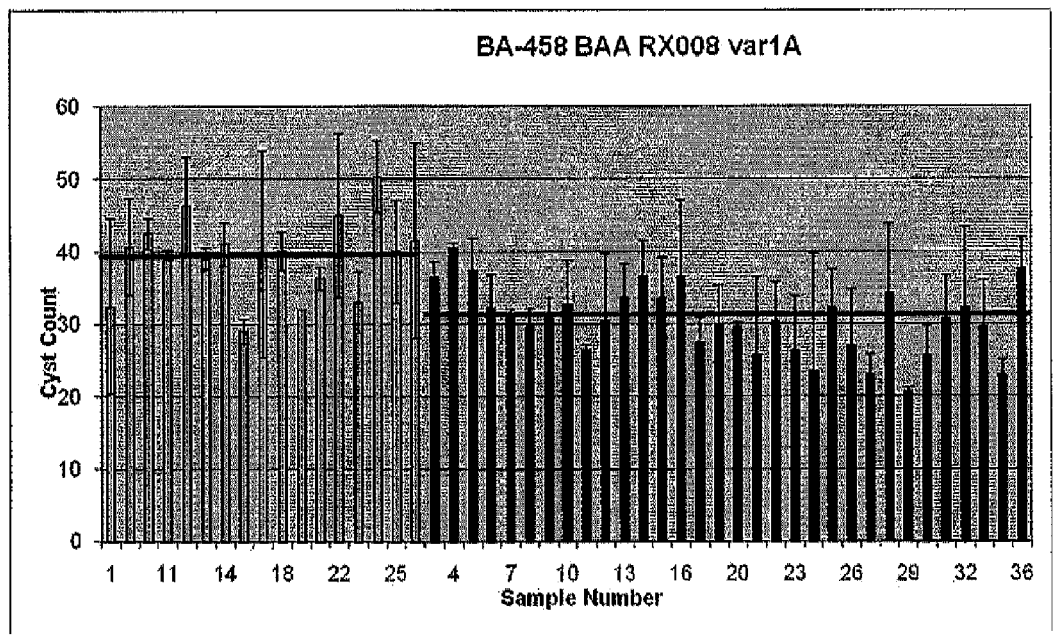
FIG. 4 depicts the results of a soybean hair root cyst-formation assay. Darker bars (on the right) represent the number of cysts formed in soybean roots transformed with a vector containing the soybean optimized RX008 nucleic acid coding sequence and challenged with soybean cyst nematodes (SCNs), while the lighter bars (on the left) represent the number of cysts formed in soybean roots transformed with an empty vector control and challenged with SCNs.

The present invention is based, in part, on the discovery and isolation of a novel *Bacillus thuringiensis* Crystal (Cry) protein. The novel Cry proteins of the invention are δ-endotoxins that exhibit toxicity to nematodes. Accordingly, the invention provides isolated δ-endotoxin polypeptides (e.g., peticidal δ-endotoxin polypeptides, particularly nematicidal δ-endotoxin polypeptides), isolated polynucleotides that encode such polypeptides, and expression cassettes comprising the presently disclosed polynucleotides. Biopesticide compositions comprising a presently disclosed δ-endotoxin polypeptide in combination with a carrier are also provided.

Compositions of the invention include isolated δ-endotoxin polypeptides having the sequence set forth in SEQ ID NO: 1, and variants and fragments thereof. Additional compositions include isolated polynucleotides comprising the sequence set forth in SEQ ID NO: 2, nucleotide sequences that encode the amino acid sequence of SEQ ID NO: 1, and variants and fragments thereof. In certain embodiments, the polynucleotides of the invention have been optimized for expression by the cells of a particular organism, e.g., nucleic acid sequences that have been back-translated (i.e., reverse translated) using plant-preferred codons based on the amino acid sequence of a polypeptide of the invention (e.g., a polypeptide having pesticidal activity).

The nucleic acids and nucleotide sequences of the invention may be used to transform an organism needing protection from an insect or nematode pest to produce the encoded δ-endotoxin polypeptides. Accordingly, the invention further provides transgenic organisms (e.g., transgenic plants and microorganisms) comprising heterologous polynucleotides that encode δ-endotoxin polypeptides of the invention (e.g., pesticidal δ-endotoxin polypeptides). Methods are provided that involve the use of such transformed organisms to impact or control pests, particularly plant pests, more particularly nematodes.

Thus, the invention involves the discovery of biodegradable pesticides and the genes that encode them, thereby providing new approaches for impacting plant pests that do not depend on the use of traditional, synthetic chemicals. As used herein, the term "plant pest" refers to any organism that can cause harm to a plant by inhibiting or slowing the growth of a plant, by damaging the tissues of a plant, by weakening the immune system of a plant, reducing the resistance of a plant to abiotic stresses, and/or by causing the premature death of the plant, etc. Relevant plant pests include, e.g., nematodes, insects, and the like.

As used herein, the term "impacting pests" refers to effecting changes in pest feeding, growth, and/or behavior at any stage of development, including but not limited to: killing the pest; retarding its growth; preventing or reducing its reproductive capability; preventing or reducing its ability to feed; and the like.

As used herein, the term "pesticidal activity" refers to the activity of an organism or a substance (such as, for example, a protein) that can be measured by, e.g., pest mortality, pest weight loss, pest repellency, and other behavioral and physical changes of a pest after feeding and exposure for an appropriate length of time. Thus, an organism or substance having pesticidal activity adversely impacts at least one measurable parameter of pest fitness. "Pesticidal proteins" are proteins that display pesticidal activity by themselves or in combination with other proteins.

In particular embodiments, the pesticidal activity exhibited by the δ-endotoxin polypeptides of the invention is nematicidal activity. As used herein, "nematicidal activity" refers to the ability to adversely impact at least one measurable parameter of nematode fitness. In certain embodiments, the nematicidal activity is measured with respect to a nematode that is a member of a *Meloidogyne*, *Heterodera*, or *Globedera* genera. In other embodiments, the nematicidal activity is measured with respect to a nematode that is selected from the group consisting of *Panagrellus redivivus*, *Distolabrellus veechi*, *Nippostrongylus brasiliensis*, and *Caenorhabditis elegans*. Evidence of nematicidal activity includes, for example, lack of pumping, inhibition of growth (i.e., small size), pale coloration, lethargy, decreased reproduction, and/or death. See, e.g., Wei et al. (2003), Proc. Nat'l Acad. Sci. 100(5):2760-65.

In other embodiments, the pesticidal activity exhibited by the δ-endotoxin polypeptides of the invention is insecticidal activity. As used herein, "insecticidal activity" refers to the ability to adversely impact insect growth or reproduction, or to kill the insect. Insecticidal activity can be measured by insect assays.

As used herein, the term "pesticidally effective amount" connotes a quantity of a substance or organism that has pesticidal activity when present in the environment of a pest. For each substance or organism, the pesticidally effective amount is determined empirically for each pest affected in a specific environment. A "nematicidally effective amount" may be used to refer to a "pesticidally effective amount" when the pest is a nematode. Similarly, an "insecticidally effective amount" may be used to refer to a "pesticidally effective amount" when the pest is an insect pest.

As used herein, the term "plant" also includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

As used herein, the terms "encoding" or "encoded" when used in the context of a specified polynucleotide mean that the polynucleotide comprises the requisite information to direct translation of the nucleotide sequence into a specified protein. The information by which a protein is encoded is specified by the use of codons. A polynucleotide encoding a protein may comprise non-translated sequences (e.g., introns) within translated regions of the polynucleotide or may lack such intervening non-translated sequences (e.g., as in cDNA).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, about 4 kb, about 3 kb, about 2 kb, about 1 kb, about 0.5 kb, or about 0.1 kb of nucleotide sequence that naturally flank the polynucleotide in genomic DNA of the cell from which the polynucleotide is derived. A protein that is substantially free of cellular material includes preparations of protein having less than about 30%, about 20%, about 10%, about 5%, or about 1% (by dry weight) of contaminating protein. When the presently disclosed pesticidal proteins or biologically active portions thereof are recombinantly produced, optimally culture medium represents less than about 30%, about 20%, about 10%, about 5%, or about 1% (by dry weight) of chemical precursors or non-protein-of-interest chemicals.

Fragments and variants of the disclosed polypeptides and polynucleotides encoding such polypeptides are also encompassed by the present invention. By "fragment" is intended a portion of the amino acid sequence of the disclosed δ-endotoxin polypeptide (i.e., a portion of the sequence of SEQ ID NO: 1) or a portion of the nucleic acid sequence of a polynucleotide encoding such a polypeptide (e.g., a portion of the sequence of SEQ ID NO: 2). Fragments of interest include those that retain pesticidal activity. For example, in certain embodiments, the polypeptide fragment is a fragment of SEQ ID NO: 1 that lacks about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, about 50, about 55, about 60, or more amino acids from the N-terminus. In certain embodiments, the polypeptide fragment is a fragment of SEQ ID NO: 1 that lacks about 50, about 100, about 150, about 200, about 250, about 300, about 350, about 400, about 450, about 500, or more amino acids from the C-terminus. In certain embodiments, the polypeptide fragment comprises an endotoxin N, an endotoxin M, and an endotoxin C domain. The three domain δ-endotoxin structure has been well characterized in the art and persons skilled in the art can readily identify polypeptide fragments containing such domains. For example, the PFam algorithm can be used to identify endotoxin domains in proteins. Analysis of SEQ ID NO: 1 using the PFam algorithm identifies an endotoxin N domain (pfam03945) starting at about amino acid residue 64 and ending at about amino acid residue 317; an endotoxin M domain (pfam00555) starting at about amino acid residue 319 and ending at about amino acid residue 526; and an endotoxin C domain (pfam03944) starting at about amino acid residue 539 and ending at about amino acid residue 684.

In certain embodiments, the polypeptide fragment comprises or consists of amino acid residues 1-1100, 1-1000, 1-900, 1-800, 1-750, 1-700, 1-690, 1-684, 1-672, 1-650, 1-600, 1-550, 1-538, or 1-526 of SEQ ID NO: 1. In certain embodiments, the polypeptide fragment comprises or consists of amino acid residues 5-1188, 10-1188, 15-1188, 20-1188, 25-1188, 30-1188, 35-1188, 40-1188, 45-1188, 50-1188, 55-1188, 60-1188, 64-1188, 75-1188, 100-1188, 150-1188, 200-1188, 250-1188, 300-1188, 318-1188, or 322-1188 of SEQ ID NO: 1. In certain embodiments, the polypeptide fragment comprises or consists of amino acid residues 2-1100, 2-900, 2-750, 2-684, 2-672, 3-1100, 3-900, 3-750, 3-684, 3-672, 4-1100, 4-900, 4-750, 4-684, 4-672, 5-1100, 5-900, 5-750, 5-684, 5-672, 6-1100, 6-900, 6-750, 6-684, 6-672, 7-1100, 7-900, 7-750, 7-684, 7-672, 8-1100, 8-900, 8-750, 8-684, 8-672, 9-1100, 9-900, 9-750, 9-684, 9-672, 10-1100, 10-900, 10-750, 10-684, 10-672, 15-1100, 15-900, 15-750, 15-684, 15-672, 20-1100, 20-900, 20-750, 20-684, 20-672, 23-1100, 23-900, 23-750, 23-684, 23-672, 25-1100, 25-900, 25-750, 25-684, 25-672, 30-1100, 30-900, 30-750, 30-684, 30-672, 64-750, 64-700, 64-690, 64-684, 64-538, 64-526, 318-684, 322-684, 322-538, or 322-526 of SEQ ID NO: 1.

The polypeptide and polypeptide fragments of the invention that exhibit nematicidal activity bind to at least one invertebrate-specific glycolipid. In certain embodiments, the glycolipid comprises the tetrasaccharide sequence N-acetylgalactosamine β1-4 N-acetylglucosamine β1-3 mannose β1-4 glucose. In certain embodiments, the glycolipid comprises the tetrasaccharide sequence N-acetylgalactosamine β1-4 N-acetylglucosamine β1-3 mannose β1-4 glucose and further comprises one or more galactose molecules. In certain embodiments, the one or more galactose molecules are part of a branched polysaccharide attached to the tetrasaccharide. Methods of detecting interactions between proteins and glycolipids are well known in the art. See, e.g., Griffitts et al. (2005), Science 307:922-25.

A polynucleotide fragment of the invention may encode a biologically active portion of a polypeptide of the invention, or it may be a fragment that can be used as a hybridization probe or PCR primer using methods disclosed below. A biologically active portion of a polypeptide of the invention can be a polypeptide fragment disclosed herein (e.g., a fragment or variant of SEQ ID NO: 1 having pesticidal activity). Alternatively, a biologically active portion of a polypeptide of the invention can be identified by isolating a portion of a polynucleotide encoding said polypeptide (e.g., a portion of the polynucleotide of SEQ ID NO: 2), expressing the encoded polypeptide fragment (e.g., by recombinant expression in vitro), and assessing the pesticidal activity of the encoded portion of the protein. Polynucleotides that are fragments of a nucleotide sequence of the invention comprise at least about 250, about 500, about 750, about 1000, about 1250, about 1500, about 1600, about 1700, about 1750, about 1800, about 1810, about 1820, about 1830, about 1840, about 1850, about 1860, about 1870, about 1880, about 1890, about 1900, about 1950, about 2000, about 2050, about 2250, about 2500, about 2750, about 3000, about 3250, about 3500, or about 3550 contiguous nucleotides. A polynucleotide fragment that encodes a biologically active portion of a polypeptide of the invention will typically encode at least about 146, about 205, about 254, about 363, about 463, about 620, about 650, about 672, or about 684 contiguous amino acids, or up to the total number of amino acids present in a full-length pesticidal protein of the invention.

Alternatively, fragments of a polynucleotide that are useful as hybridization probes generally do not encode polypeptide fragments retaining biological activity. Thus, fragments of a nucleotide sequence may range from at least about 20 nucleotides, about 50 nucleotides, about 100 nucleotides, and up to the full-length polynucleotide encoding the presently disclosed proteins.

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites within the native polynucleotide; and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of SEQ ID NO: 1. Naturally occurring allelic variants can be identified with the use of well-known molecular biology techniques, including, for example, with polymerase chain reaction (PCR) and hybridization techniques as outlined elsewhere herein. Variant polynucleotides also include synthetically derived polynucleotides, such as those generated, for example, by using site-directed mutagenesis but which still encode a protein of the invention or a fragment thereof. Generally, variants of a particular polynucleotide of the invention will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 1 or a fragment thereof (e.g., a biologically active fragment) are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 90%, about 91%, about 92%, about 93%, about 94%, about 95%, about 96%, about 97%, about 98%, about 99% or more sequence identity.

"Variant" polypeptide is intended to mean a protein derived from the native protein or a fragment thereof by deletion (so-called truncation) of one or more amino acids at the N-terminal and/or C-terminal end of the native protein; deletion or addition of one or more amino acids at one or more internal sites in the native protein; and/or substitution of one or more amino acids at one or more sites in the native protein.

Variant polypeptides encompassed by the present invention are biologically active, that is they continue to possess a desired biological activity of the native protein. For example, in certain embodiments, polypeptide variants of the invention have pesticidal activity (e.g., nematicidal and/or insecticidal activity). In certain embodiments, polypeptide variants of the invention bind to at least one invertebrate specific glycolipid. In certain embodiments, the glycolipid comprises the tetrasaccharide sequence N-acetylgalactosamine β1-4 N-acetylglucosamine β1-3 mannose β1-4 glucose. In certain embodiments, the glycolipid comprises the tetrasaccharide sequence N-acetylgalactosamine β1-4 N-acetylglucosamine β1-3 mannose β1-4 glucose and further comprises one or more galactose molecules. In certain embodiments, the one or more galactose molecules are part of a branched polysaccharide attached to the tetrasaccharide. Polypeptide variants of the invention may result from, for example, genetic polymorphism or from human manipulation. In general, biologically active variants of a polypeptide of the invention will have at least about 90%, about 91%, about 92%, about 93%, about 94%, about 95%, about 96%, about 97%, about 98%, about 99% or more sequence identity to the amino acid sequence for the native protein, as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of SEQ ID NO: 1 can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired biological activity (e.g., pesticidal and/or glycolipid-binding activity). Obviously, the mutations that will be made in the DNA encoding the variant must not place the sequence out of reading frame and optimally will not create complementary regions that could produce secondary mRNA structure.

The deletions, insertions, and substitutions of the protein sequences encompassed herein are not expected to produce radical changes in the characteristics of the protein. Sequence variants likely to have conserved structure and function can be identified by conventional methods. For example, PFam and other domain identification tools can be used to identify amino acids required for the proper folding of protein domains, such as the endotoxin N, endotoxin M, and endotoxin C domains. Conserved or conservatively substituted hydrophobic residues found in protein domains that have the same structure but differ in function are often involved in determining secondary and tertiary structure. Multi-sequence alignment tools can be used to identify conserved amino acids in protein domains having related structure and function (e.g., additional Cry proteins having nematicidal activity have been identified, including Cry 14A, Cry5B, and Cry21A; see Wei et al. (2003), Proc. Nat'l Acad. Sci. 200(5):2760-65). Amino acid residues conserved between structurally and functionally related domains but not identified as critical for the proper folding of the domain are more likely to relate to the function of the protein domain. In general, variation of amino acids at positions that are neither structurally nor functionally conserved typically results in functional variants; variation of amino acids at positions that are structurally and/or functionally conserved is more constrained, but is sometimes still permissible (e.g., if substitutions are allowed, typically only conservative substitutions are permissible, although certain non-conservative substitutions may be permissible). The endotoxin N domain has been assigned the PFam designation pfam03945; the endotoxin M domain has been assigned the PFam designation pfam00555; and the endotoxin C domain has been assigned PFam designation pfam03944.

Additionally, structural prediction tools such as CABS, ESyPred3D, HHpred, ROBETTA, and WHAT IF can be used to model the structure of protein domains based upon known crystal structures, allowing (1) the identification of amino acids located at the surface of a protein domain, and (2) in silico evaluation of the potential effects of introducing amino acid changes into a sequence. Non-conserved amino acids located at the surface of a protein domain are typically amenable to a range of different amino acid substitutions, whereas conserved amino acids located at the surface of a protein domain are often involved in important interactions (e.g., protein-protein, protein-carbohydrate, protein-lipid, etc.) and thus the types of permissible substitutions are more constrained (e.g., if substitutions are allowed, typically only conservative substitutions are permissible, although certain non-conservative substitutions may be permissible). Each of the endotoxin domains of SEQ ID NO: 1 can be structurally modeled, e.g., using the structure of Cry1Aa, Cry2Aa, Cry3Aa, Cry3Bb, Cry4Aa, or Cry4Bb (see Bravo et al. (2007), Toxicon. 49(4):423-35).

Accordingly, using conventional sequence analysis tools, structural prediction tools, and/or screening methods disclosed in the present application, polypeptide variants of the invention having conserved structure and function relative to SEQ ID NO: 1 can be identified and tested for function. Even when it is difficult to predict the exact effect of the substitution, deletion, or insertion in advance of doing so, one skilled in the art will appreciate that the effect can be evaluated by routine screening assays. That is, the activity can be evaluated by assays that measure pesticidal activity, such as nematicidal activity, and/or glycolipid-binding activity. See, e.g., Wei et al. (2003), Prot. Nat'l Acad. Sci. 100(5):2760-65; Griffitts et al. (2005), Science 307:922-25.

Variant polynucleotides and proteins also encompass sequences and proteins derived from a mutagenic and recombinogenic procedure such as DNA shuffling. With such a procedure, one or more different pesticidal protein coding sequences can be manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a gene encoding the δ-endotoxin of SEQ ID NO: 1 and other known pesticidal δ-endotoxin genes, such as, for example, Cry14A, Cry21A, Cry5B, and other genes encoding δ-endotoxins, to obtain a new gene coding for a protein with an improved property of interest, such as increased pesticidal (e.g., nematicidal) activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other strains of *Bacillus thuringiensis* or other *Bacillus* species. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Functions of orthologs are often highly conserved among species. Thus, isolated polynucleotides that encode for a pesticidal and/or glycolipid-binding protein and which hybridize under stringent conditions to the sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed, e.g., in Sambrook et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and (d) "percentage of sequence identity."

(a) As used herein, a "reference sequence" is a defined sequence used as a basis for sequence comparison. A reference sequence may be a subset or the entirety of a specified sequence; for example, a segment of a full-length cDNA or gene sequence (e.g., a segment that encodes a protein structural domain), the complete cDNA or gene sequence, a segment of a full-length protein (e.g., a structural domain), or the full-length protein.

(b) As used herein, "comparison window" makes reference to a contiguous and specified segment of a polynucleotide or polypeptide sequence, wherein the sequence in the comparison window may comprise additions or deletions (i.e., gaps) compared to the reference sequence (which does not comprise additions or deletions) for optimal alignment of the two polynucleotides or polypeptides. For polynucleotides, the comparison window is typically at least 20 contiguous nucleotides in length, and optionally can be 30, 40, 50, 100, or longer. For polypeptides, a useful comparison window is either a length corresponding to the full-length protein or an active fragment thereof, such as a structural domain, a functionally conserved sequence, or a sequence involved in important binding interactions.

(c) As used herein, "sequence identity" or "identity" in the context of two polynucleotides or polypeptide sequences makes reference to the residues in the two sequences that are the same when aligned for maximum correspondence over a specified comparison window.

(d) As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877. Computer implementations of these mathematical algorithms can be utilized for comparison of sequences to determine sequence identity. Such implementations include, but are not limited to: CLUSTAL, ALIGN, GAP, BESTFIT (uses the local homology algorithm of Smith and Waterman (1981) to find the best segment of similarity between two sequences), BLAST (Basic Local Alignment Search Tool), PSI-BLAST, FASTA, and TFASTA. Alignments using these programs can be performed using the default parameters. For closely related sequences, alignment may also be performed manually by inspection.

The polynucleotides of the present invention can be expressed in a host cell, such as a bacterial, fungal, yeast, insect, mammalian, or preferably plant cells. By "host cell" is meant a cell which comprises a heterologous polynucleotide of the invention. Host cells may be prokaryotic cells, such as *E. coli*, or eukaryotic cells, such as yeast, insect, amphibian, or mammalian cells. In some embodiments, host cells are monocotyledonous or dicotyledonous plant cells.

The polynucleotides of the invention can be provided in expression cassettes for expression in a host cell. The expression cassettes of the invention find use in generating transformed plants, plant cells, and microorganisms and in practicing the methods for inducing pest resistance disclosed herein. The cassette will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes a polypeptide (e.g., a pesticidal and/or glycolipid binding polypeptide of the invention) to be under the transcriptional regulation of the regulatory regions.

The expression cassette will include in the 5'-3' direction of transcription, a transcriptional and translational initiation region (i.e., a promoter), a polynucleotide of the invention, and a transcriptional and translational termination region (i.e., termination region) functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato proteinase inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

Where appropriate, the polynucleotides may be optimized for increased expression in the transformed organism. For example, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. A wide range of plant promoters are discussed in the review of Potenza et al. (2004) *In Vitro Cell Dev Biol-Plant* 40:1-22, herein incorporated by reference. For example, the nucleic acids can be combined with constitutive, tissue-preferred, or other promoters for expression in plants. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos.

5,608,149; 5,608,144; 5,604,121; 5,569,597; 5,466,785; 5,399,680; 5,268,463; 5,608,142; and 6,177,611.

Generally, it will be beneficial to express the gene from an inducible promoter, such as a pest-inducible promoter. For example, the promoter can be a nematode-inducible promoter or a wound-inducible promoter. See, for example, U.S. Pat. No. 5,750,386 (nematode-inducible); potato proteinase inhibitor (pin II) gene (Ryan (1990) Ann. Rev. Phytopath. 28:425-449; Duan et al. (1996) Nature Biotechnology 14:494-498); wun1 and wun2, U.S. Pat. No. 5,428,148; win1 and win2 (Stanford et al. (1989) Mol. Gen. Genet. 215:200-208); systemin (McGurl et al. (1992) Science 225:1570-1573); WIP1 (Rohmeier et al. (1993) Plant Mol. Biol. 22:783-792; Eckelkamp et al. (1993) FEBS Letters 323:73-76); MPI gene (Corderok et al. (1994) Plant J. 6(2):141-150); and the like, herein incorporated by reference.

Tissue-preferred promoters can be utilized to target enhanced expression of the pesticidal polypeptides of the invention within a particular plant tissue. For example, a tissue-preferred promoter may be used to express a polypeptide of the invention in a plant tissue where disease resistance is particularly important, such as, for example, the roots or the leaves. Tissue-preferred promoters include Yamamoto et al. (1997) Plant J. 12(2):255-265; Kawamata et al. (1997) Plant Cell Physiol. 38(7):792-803; Hansen et al. (1997) Mol. Gen. Genet. 254(3):337-343; Russell et al. (1997) Transgenic Res. 6(2):157-168; Rinehart et al. (1996) Plant Physiol. 112(3): 1331-1341; Van Camp et al. (1996) Plant Physiol. 112(2): 525-535; Canevascini et al. (1996) Plant Physiol. 112(2): 513-524; Yamamoto et al. (1994) Plant Cell Physiol. 35(5): 773-778; Lam (1994) Results Probl. Cell Differ. 20:181-196; Orozco et al. (1993) Plant Mol. Biol. 23(6):1129-1138; Matsuoka et al. (1993) Proc Natl. Acad. Sci. USA 90(20):9586-9590; and Guevara-Garcia et al. (1993) Plant J. 4(3):495-505. Such promoters can be modified, if necessary, for weak expression.

Leaf-preferred promoters are known in the art. See, for example, Yamamoto et al. (1997) Plant J. 12(2):255-265; Kwon et al. (1994) Plant Physiol. 105:357-67; Yamamoto et al. (1994) Plant Cell Physiol. 35(5):773-778; Gotor et al. (1993) Plant J. 3:509-18; Orozco et al. (1993) Plant Mol. Biol. 23(6):1129-1138; and Matsuoka et al. (1993) Proc. Natl. Acad. Sci. USA 90(20):9586-9590.

Root-preferred promoters are known and can be selected from the many available from the literature or isolated de novo from various compatible species. See, for example, Hire et al. (1992) Plant Mol. Biol. 20(2):207-218 (soybean root-specific glutamine synthetase gene); Keller and Baumgartner (1991) Plant Cell 3(10):1051-1061 (root-specific control element in the GRP 1.8 gene of French bean); Sanger et al. (1990) Plant Mol. Biol. 14(3):433-443 (root-specific promoter of the mannopine synthase (MAS) gene of Agrobacterium tumefaciens); and Miao et al. (1991) Plant Cell 3(1):11-22 (full-length cDNA clone encoding cytosolic glutamine synthetase (GS), which is expressed in roots and root nodules of soybean). See also Bogusz et al. (1990) Plant Cell 2(7): 633-641, where two root-specific promoters isolated from hemoglobin genes from the nitrogen-fixing nonlegume Parasponia andersonii and the related non-nitrogen-fixing nonlegume Trema tomentosa are described. The promoters of these genes were linked to a β-glucuronidase reporter gene and introduced into both the nonlegume Nicotiana tabacum and the legume Lotus corniculatus, and in both instances root-specific promoter activity was preserved. Leach and Aoyagi (1991) describe their analysis of the promoters of the highly expressed rolC and rolD root-inducing genes of Agrobacterium rhizogenes (see Plant Science (Limerick) 79(1):69-76). They concluded that enhancer and tissue-preferred DNA determinants are dissociated in those promoters. Teeri et al. (1989) used gene fusion to lacZ to show that the Agrobacterium T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see EMBO J. 8(2):343-350). The TR1' gene, fused to nptII (neomycin phosphotransferase II) showed similar characteristics. Additional root-preferred promoters include the VfENOD-GRP3 gene promoter (Kuster et al. (1995) Plant Mol. Biol. 29(4):759-772); and rolB promoter (Capana et al. (1994) Plant Mol. Biol. 25(4):681-691. See also U.S. Pat. Nos. 5,837,876; 5,750,386; 5,633,363; 5,459,252; 5,401,836; 5,110,732; and 5,023,179.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) Biotechnol Bioeng 85:610-9 and Fetter et al. (2004) Plant Cell 16:215-28), cyan florescent protein (CYP) (Bolte et al. (2004) J. Cell Science 117:943-54 and Kato et al. (2002) Plant Physiol 129:913-42), and yellow florescent protein (PhiYFP™ from Evrogen, see, Bolte et al. (2004) J. Cell Science 117:943-54). For additional selectable markers, see generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Aci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl. Acad. Sci. USA 89:3952-3956; Baim et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference.

The above list of selectable marker genes is not meant to be limiting. Any selectable marker gene can be used in the present invention.

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods. Polypeptides can also be introduced to a plant in such a manner that they gain access to the interior of the plant cell or remain external to the cell but in close contact with it.

"Stable transformation" is intended to mean that the nucleotide construct introduced into a plant integrates into the genome of the plant and is capable of being inherited by the progeny thereof "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055 and U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; and, U.S. Pat. No. 5,932, 782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Bio/technology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the sequences of the invention can be provided to a plant using a variety of transient transformation methods. Such transient transformation methods include, but are not limited to, the introduction of the protein or variants and fragments thereof directly into the plant or the introduction of a corresponding transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it's released to become integrated into the genome is greatly reduced. Such methods include the use particles coated with polyethylimine (PEI; Sigma # P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the pesticidal polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889, 190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in a transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

In certain embodiments, the polynucleotides of the present invention can be stacked with any combination of polynucleotide sequences of interest in order to create plants with a desired phenotype. For example, the polynucleotides of the present invention may be stacked with other pesticidal genes and the like. The combinations generated can also include multiple copies of any one of the polynucleotides of interest. The polynucleotides of the present invention can also be stacked with any other gene or combination of genes to produce plants with a variety of desired trait combinations including, but not limited to, traits desirable for animal feed such as high oil genes (e.g., U.S. Pat. No. 6,232,529); balanced amino acids (e.g., hordothionins (U.S. Pat. Nos. 5,990, 389; 5,885,801; 5,885,802; and 5,703,409); barley high lysine (Williamson et al. (1987) *Eur. J. Biochem.* 165:99-106; and WO 98/20122) and high methionine proteins (Pedersen et al. (1986) *J. Biol. Chem.* 261:6279; Kirihara et al. (1988) *Gene* 71:359; and Musumura et al. (1989) *Plant Mol. Biol.* 12:123)); increased digestibility (e.g., modified storage proteins (U.S. Pat. No. 6,858,778); and thioredoxins (U.S. Pat. No. 7,009,087)); the disclosures of which are herein incorporated by reference.

The polynucleotides of the present invention can also be stacked with traits desirable for insect, disease, or herbicide resistance (e.g., other *Bacillus thuringiensis* toxic proteins (U.S. Pat. Nos. 5,366,892; 5,747,450; 5,737,514; 5,723,756; 5,593,881; Geiser et al. (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (e.g., the EPSPS gene and the GAT gene; see, for example U.S. Publication No. 20040082770 and WO 03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)); the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g., WO 99/61619, WO 00/17364, and WO 99/25821); the disclosures of which are herein incorporated by reference.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The present invention may be used to induce pest resistance or protect from pest attack any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean and plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas.

Beans include guar, locust bean, fenugreek, soybean, garden beans, cowpea, mungbean, lima bean, fava bean, lentils, chickpea, etc.

In particular aspects, methods for inducing pest resistance in a plant comprise introducing into a plant at least one polynucleotide, wherein the polynucleotide comprises a nucleotide sequence encoding a pesticidal and/or glycolipid-binding δ-endotoxin polypeptide of the invention. The polynucleotide is operably linked to a promoter that drives expression in the plant. The plant expresses the pesticidal and/or glycolipid-binding polypeptide, thereby exposing the pest to the polypeptide at the site of attack. In particular embodiments, the δ-endotoxin polypeptides have nematicidal activity and the pest is a nematode. Expression of a δ-endotoxin polypeptide of the invention may be targeted to specific plant tissues where pest resistance is particularly important. Such tissue-preferred expression may be accomplished by, e.g., root-preferred, leaf-preferred, vascular tissue-preferred, stalk-preferred, or seed-preferred promoters. For nematode control, root-preferred promoters are typically optimal.

The compositions of the invention find further use in methods directed to protecting a plant from a pest or pathogen. "Protecting a plant from a pest or pathogen" is intended to mean killing the pest or pathogen or preventing or limiting disease formation on a plant. In some embodiments, a composition comprising a polypeptide of the invention and a carrier is applied directly to the environment of a plant pest or pathogen, such as, for example, on a plant or in the soil or other growth medium surrounding the roots of the plant, in order to protect the plant from pest and/or pathogen attack. Microorganisms comprising a polynucleotide encoding a polypeptide of the invention and methods of using them to protect a plant from a pest or pathogen are further provided. In some embodiments, the transformed microorganism is applied directly to a plant or to the soil in which a plant grows.

Biopesticide compositions, particularly nematicidal and insecticidal compositions, are thus encompassed by the present invention. Biopesticide compositions may comprise pesticidal δ-endotoxin polypeptides or microorganisms comprising a heterologous polynucleotide that encodes a pesticidal δ-endotoxin polypeptide. The biopesticide compositions of the invention may be applied to the environment of a plant pest or pathogen, as described herein below, thereby protecting a plant from pest and/or pathogen attack. Moreover, a biopesticide composition can be formulated with an acceptable carrier that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

The biospesticide compositions find further use in the decontamination of plant pest and/or pathogens during the processing of grain for animal or human food consumption; during the processing of feedstuffs, and during the processing of plant material for silage. In this embodiment, the biopesticide compositions of the invention are presented to grain, plant material for silage, or a contaminated food crop, or during an appropriate stage of the processing procedure, in amounts effective for nematicidal and/or insecticidal activity.

A polynucleotide encoding a pesticidal, particularly nematicidal or insecticidal, δ-endotoxin polypeptide of the invention may be introduced into any suitable microbial host according to standard methods in the art. For example, microorganism hosts that are known to occupy the "phytosphere" (phylloplane, phyllosphere, rhizosphere, and/or rhizoplane) of one or more crops of interest may be selected. These microorganisms are selected so as to be capable of successfully competing in the particular environment with the wild-type microorganisms, and to provide for stable maintenance and expression of the gene expressing the pesticidal protein.

Prokaryotic cells may be used as hosts for expression to create the biopesticide compositions. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived PL promoter and N-gene ribosome binding site (Simatake and Rosenberg (1981) *Nature* 292:128). Examples of selection markers for *E. coli* include, for example, genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva et al. (1983) *Gene* 22:229-235 and Mosbach et al. (1983) *Nature* 302:543-545).

Other suitable microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinelandii* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

Other illustrative prokaryotes, both Gram-negative and gram-positive, include *Enterobacteriaceae*, such as *Escherichia, Erwinia, Shigella, Salmonella*, and *Proteus; Bacillaceae; Rhizobiaceae*, such as *Rhizobium; Spirillaceae*, such as photobacterium, *Zymomonas, Serratia, Aeromonas, Vibrio, Desulfovibrio, Spirillum; Lactobacillaceae; Pseudomonadaceae*, such as *Pseudomonas* and *Acetobacter; Azotobacteraceae* and *Nitrobacteraceae*. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Microbial host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Fla-* vobacterium spp., and other such organisms, including *Pseudomonas aeruginosa, Pseudomonas fluorescens, Saccharomyces cerevisiae, Bacillus thuringiensis, Escherichia coli, Bacillus subtilis*, and the like.

Polynucleotides encoding the pesticidal δ-endotoxin polypeptides of the invention can be introduced into microorganisms that multiply on plants (epiphytes) to deliver pesticidal δ-endotoxin proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Polynucleotides encoding the pesticidal polypeptides of the invention can be introduced into a root-colonizing *Bacillus cereus* by standard methods known in the art.

Polynucleotides encoding pesticidal δ-endotoxin polypeptides can be introduced, for example, into the root-colonizing *Bacillus* by means of electrotransformation. Specifically, polynucleotides encoding the pesticidal δ-endotoxin proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein can, for example, be transformed into the root-colonizing *Bacillus* by means of electroporation (Lerecius et al. (1989) *FEMS Microbiol. Letts.* 60: 211-218).

Methods are provided for protecting a plant from a pest comprising applying an effective amount of a pesticidal δ-endotoxin polypeptide or biopesticide composition of the invention to the environment of the pest. "Effective amount" is intended to mean an amount of a protein or composition sufficient to control a pest. The pesticidal proteins and compositions can be applied to the environment of the pest by methods known to those of ordinary skill in the art.

Prior to the application of a biopesticide composition of the invention to an area of cultivation, the environment can be evaluated to determine if the pest of interest is present or if conditions are conducive to pest growth or infestation. As used herein, an "area of cultivation" comprises any region in which one desires to grow a plant. Such areas of cultivations include, but are not limited to, a field in which a plant is cultivated (such as a crop field, a sod field, a tree field, a managed forest, a field for culturing fruits and vegetables, etc), a greenhouse, a growth chamber, etc. Evaluation of the environment can aid in determining the effective amount of the pesticidal δ-endotoxin polypeptide or biopesticide composition of the invention needed to control a pest within an area of cultivation.

Environmental conditions that can be evaluated include, but are not limited to, ground and surface water pollution concerns, intended use of the crop, crop tolerance, soil residuals, weeds present in area of cultivation, humidity, soil texture, pH of soil, amount of organic matter in soil, water content of soil, application equipment, and tillage practices. Following the evaluation of the environmental conditions, an effective amount of a pesticidal δ-endotoxin polypeptide or biopesticide composition of the invention can be applied to the crop, crop part, seed of the crop or area of cultivation.

The biopesticide compositions of the invention may be obtained by the addition of a surface-active agent, an inert carrier, a preservative, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the pesticidal proteins, more particularly nematicidal or insecticidal proteins, of the present invention include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphthalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The biopesticide compositions of the present invention can be in a suitable form for direct application or as a concentrate of primary composition that requires dilution with a suitable quantity of water or other diluent before application. The concentration of the pesticidal polypeptide will vary depending upon the nature of the particular formulation, specifically, whether it is a concentrate or to be used directly. The composition contains 1 to 98% of a solid or liquid inert carrier, and 0 to 50%, optimally 0.1 to 50% of a surfactant. These compositions will be administered at the labeled rate for the commercial product, optimally about 0.01 lb-5.0 lb. per acre when in dry form and at about 0.01 pts.-10 pts. per acre when in liquid form.

The biopesticide compositions of the invention can be applied to the environment of a plant pathogen by, for example, spraying, atomizing, dusting, scattering, coating or pouring, introducing into or on the soil, introducing into irrigation water, by seed treatment or general application or dusting at the time when the pathogen has begun to appear or before the appearance of pests as a protective measure. For example, the pesticidal protein and/or transformed microorganisms of the invention may be mixed with grain to protect the grain during storage. It is generally important to obtain good control of pests in the early stages of plant growth, as this is the time when the plant can be most severely damaged. In one embodiment of the invention, the composition is applied directly to the soil, at a time of planting, in granular form of a composition of a carrier and pesticidal polypeptides or transformed microorganisms of the invention. Another embodiment is a granular form of a composition comprising an agrochemical such as, for example, a herbicide, an insecticide, a fertilizer, an inert carrier, and pesticidal polypeptides or transformed microorganisms of the invention.

One of skill in the art will appreciate that the compositions and methods disclosed herein can be used with other compositions and methods available in the art for protecting plants from pathogen attack. For example, methods of the invention can comprise the use of one or more herbicides, insecticides, fungicides, nematocides, bactericides, acaricides, growth regulators, chemosterilants, semiochemicals, repellents, attractants, pheromones, feeding stimulants or other biologically active compounds or entomopathogenic bacteria, virus, or fungi to form a multi-component mixture giving an even broader spectrum of agricultural protection. General references for these agricultural protectants include The Pesticide Manual, 13th Edition, C. D. S. Tomlin, Ed., British Crop Protection Council, Farnham, Surrey, U.K., 2003 and The BioPesticide Manual, 2nd Edition, L. G. Copping, Ed., British Crop Protection Council, Farnham, Surrey, U.K., 2001.

The embodiments of the present invention may be effective against a variety of plant pathogens. Pathogens of the invention include, but are not limited to, nematodes, insects, viruses or viroids, bacteria, fungi, and the like. Nematodes include plant parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

Insects of the order Lepidoptera include, but are not limited to, armyworms, cutworms, loopers, and heliothines in the family Noctuidae *Agrotis ipsilon* Hufnagel (black cutworm); *A. orthogonia* Morrison (western cutworm); *A. segetum* Denis & Schiffermüller (turnip moth); *A. subterranea* Fabricius (granulate cutworm); *Alabama argillacea* Hübner (cotton leaf worm); *Anticarsia gemmatalis* Hübner (velvetbean caterpillar); *Athetis mindara* Barnes and McDunnough (rough skinned cutworm); *Earias insulana* Boisduval (spiny bollworm); *E. vittella* Fabricius (spotted bollworm); *Egira* (*Xylomyges*) *curialis* Grote (citrus cutworm); *Euxoa messoria* Harris (darksided cutworm); *Helicoverpa armigera* Hübner (American bollworm); *H. zea* Boddie (corn earworm or cotton bollworm); *Heliothis virescens* Fabricius (tobacco budworm); *Hypena scabra* Fabricius (green cloverworm); *Hyponeuma taltula* Schaus; (*Mamestra configurata* Walker (bertha armyworm); *M. brassicae* Linnaeus (cabbage moth); *Melanchra picta* Harris (zebra caterpillar); *Mocis latipes* Guenée (small mocis moth); *Pseudaletia unipuncta* Haworth (armyworm); *Pseudoplusia includens* Walker (soybean looper); *Richia albicosta* Smith (Western bean cutworm); *Spodoptera frugiperda* JE Smith (fall armyworm); *S. exigua* Hübner (beet armyworm); *S. litura* Fabricius (tobacco cutworm, cluster caterpillar); *Trichoplusia ni* Hübner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stemp borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea flavipennella* Box; *D. grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hübner (tobacco (cacao) moth); *Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower moth); *Loxostege sticticalis* Linnaeus (beet webworm); *Maruca testulalis* Geyer (bean pod borer); *Orthaga thyrisalis* Walker (tea tree web moth); *Ostrinia nubilalis* Hübner (European corn borer); *Plodia interpunctella* Hübner (Indian meal moth); *Scirpophaga incertulas* Walker (yellow stem borer); *Udea rubigalis* Guenée (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rösslerstamm (summer fruit tortrix moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hübner (vine moth); *Grapholita molesta* Busck (oriental fruit moth); *Lobesia botrana* Denis & Schiffermüller (European grape vine moth); *Platynota flavedana* Clemens (variegated leafroller); *P. stultana* Walsingham (omnivorous leafroller); *Spilonota ocellana* Denis & Schiffermüller (eyespotted bud moth); and *Suleima helianthana* Riley (sunflower bud moth).

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Méneville (grapeleaf skeletonizer); *Heliothis subflexa* Guenée; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Telchin licus* Drury (giant sugarcane borer); *Thaumetopoea pityocampa* Schiffermüller (pine processionary caterpillar); *Tineola bisselliella* Hummel (webbing clothesmoth); *Tuta absoluta* Meyrick (tomato leafminer) and *Yponomeuta padella* Linnaeus (ermine moth).

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (Diaprepes root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus sericeus* Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *S. livis* Vaurie (sugarcane weevil); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape colaspis); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculata* Olivier (southern masked chafer, white grub); *Dermolepida albohirtum* Waterhouse (Greyback cane beetle); *Euetheola humilis* rugiceps LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leafmining buprestid beetle).

Adults and immatures of the order Diptera are of interest, including leafminers *Agromyza parvicornis* Loew (corn blotch leafminer); midges including, but not limited to: *Contarinia sorghicola* Coquillett (sorghum midge); *Mayetiola destructor* Say (Hessian fly); *Neolasioptera murtfeldtiana* Felt, (sunflower seed midge); *Sitodiplosis mosellana* Géhin (wheat midge); fruit flies (Tephritidae), *Oscinella frit* Linnaeus (frit flies); maggots including, but not limited to: *Delia* spp. including *Delia platura* Meigen (seedcorn maggot); *D. coarctate* Fallen (wheat bulb fly); *Fannia canicularis* Linnaeus, *F. femoralis* Stein (lesser house flies); *Meromyza americana* Fitch (wheat stem maggot); *Musca domestica* Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are those of the order Hemiptera such as, but not limited to, the following families: Adelgidae, Aleyrodidae, Aphididae, Asterolecamidae, Cercopidae, Cicadellidae, Cicadidae, Cixiidae, Coccidae, Coreidae, Dactylopiidae, Delphacidae, Diaspididae, Eriococcidae, Flatidae, Fulgoridae, Issidae, Lygaeidae, Margarodidae, Membracidae, Miridae, Ortheziidae, Pentatomidae, Phoenicococcidae, Phylloxeridae, Pseudococcidae, Psyllidae, Pyrrhocoridae and Tingidae.

Agronomically important members from the order Hemiptera include, but are not limited to: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacaspis tegalensis* Zehntner (sugarcane scale); *Aulacorthum solani* Kaltenbach (foxglove aphid); *Bemisia tabaci* Gennadius (tobacco whitefly, sweetpotato whitefly); *B. argentifolii* Bellows & Perring (silverleaf whitefly); *Blissus leucopterus leucopterus* Say (chinch bug); *Blostomatidae* spp.; *Brevico-*

*ryne brassicae* Linnaeus (cabbage aphid); *Cacopsylla pyricola* Foerster (pear psylla); *Calocoris norvegicus* Gmelin (potato capsid bug); *Chaetosiphon fragaefolii* Cockerell (strawberry aphid); *Cimicidae* spp.; *Coreidae* spp.; *Corythuca gossypii* Fabricius (cotton lace bug); *Cyrtopeltis modesta* Distant (tomato bug); *C. notatus* Distant (suckfly); *Deois flavopicta* Stål (spittlebug); *Dialeurodes citri* Ashmead (citrus whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schäffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *E. variolarius* Palisot de Beauvois (one-spotted stink bug); *Graptostethus* spp. (complex of seed bugs); and *Hyalopterus pruni* Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *M. posticata* Stål (little cicada of sugarcane); *Melanaphis sacchari* Zehntner (sugarcane aphid); *Melanaspis glomerate* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; *Pemphigus* spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan phylloxera); *Planococcus citri* Risso (citrus mealybug); *Plesiocoris rugicollis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); *Pyrrhocoridae* spp.; *Quadraspidiotus perniciosus* Comstock (San Jose scale); *Reduviidae* spp.; *Rhopalosiphum maidis* Fitch (corn leaf aphid); *R. padi* Linnaeus (bird cherry-oat aphid); *Saccharicoccus sacchari* Cockerell (pink sugarcane mealybug); *Scaptacoris castanea* Perty (brown root stink bug); *Schizaphis graminum* Rondani (greenbug); *Sipha flava* Forbes (yellow sugarcane aphid); *Sitobion avenae* Fabricius (English grain aphid); *Sogatella furcifera* Horvath (white-backed planthopper); *Sogatodes oryzicola* Muir (rice delphacid); *Spanagonicus albofasciatus* Reuter (whitemarked fleahopper); *Therioaphis maculata* Buckton (spotted alfalfa aphid); *Tinidae* spp.; *Toxoptera aurantii* Boyer de Fonscolombe (black citrus aphid); and *T. citricida* Kirkaldy (brown citrus aphid); *Trialeurodes abutiloneus* (bandedwinged whitefly) and *T. vaporariorum* Westwood (greenhouse whitefly); *Trioza diospyri* Ashmead (persimmon psylla); and *Typhlocyba pomaria* McAtee (white apple leafhopper).

Also included are adults and larvae of the order Acari (mites) such as *Aceria tosichella* Keifer (wheat curl mite); *Panonychus ulmi* Koch (European red mite); *Petrobia latens* Müller (brown wheat mite); *Steneotarsonemus bancrofti* Michael (sugarcane stalk mite); spider mites and red mites in the family Tetranychidae, *Oligonychus grypus* Baker & Pritchard, *O. indicus* Hirst (sugarcane leaf mite), *O. pratensis* Banks (Banks grass mite), *O. stickneyi* McGregor (sugarcane spider mite); *Tetranychus urticae* Koch (two spotted spider mite); *T. mcdanieli* McGregor (McDaniel mite); *T. cinnabarinus* Boisduval (carmine spider mite); *T. turkestani* Ugarov & Nikolski (strawberry spider mite), flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede). In addition, insect pests of the order Isoptera are of interest, including those of the termitidae family, such as, but not limited to, *Cornitermes cumulans* Kollar, *Cylindrotermes nordenskioeldi* Holmgren and *Pseudacanthotermes militaris* Hagen (sugarcane termite); as well as those in the Rhinotermitidae family including, but not limited to *Heterotermes tenuis* Hagen. Insects of the order Thysanoptera are also of interest, including but not limited to thrips, such as *Stenchaetothrips minutus* van Deventer (sugarcane thrips).

In an embodiment of the invention, the compositions of the invention may be used as a pharmaceutical composition for treatment of parasites (e.g., namatode parasites) in humans and other animals. Examples of nematode parasites include, but are not limited to, ascarids (*Ascaris*), filarias (e.g., *Onchocerca volvulus*), hookworms, pinworms (*Enterobius*), whipworms (e.g., *Trichuris trichiura*), *Trichinella spiralis, Baylisascaris, Dirofilaria immitis, Haemonchus contortus, Nippostrongylus brasiliensis, Ancylostoma duodenale*, and *Necator americanus*. In some of these embodiments, the pesticidal polypeptide is combined with a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds also can be incorporated into the compositions.

The presently disclosed pharmaceutical compositions may be administered to a patient through numerous means. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 µg/kg to about 15 mg/kg (e.g., 0.1 to 20 mg/kg) of active compound is an initial candidate dosage for administration to the patient, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

"Treatment" is herein defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A "therapeutic agent" comprises, but is not limited to, the polypeptides and pharmaceutical compositions of the invention.

The δ-endotoxin polypeptides of the invention can be used for any application including coating surfaces to target parasites. In this manner, target parasites include parasitic nematodes that infect humans and animals (e.g., domestic livestock). Surfaces that might be coated with the pesticidal compositions of the invention include carpets and sterile medical facilities. Polymer bound polypeptides of the invention may be used to coat surfaces. Methods for incorporating compositions with antimicrobial properties into polymers are known in the art. See U.S. Pat. No. 5,847,047 herein incorporated by reference.

The articles "a" and "an" are used herein to refer to one or more than one (i.e., to at least one) of the grammatical object of the article. By way of example, "a polypeptide" is understood to represent one or more polypeptides. As such, the terms "a" (or "an"), "one or more," and "at least one" can be used interchangeably herein.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Unless defined otherwise, all technical and scientific terms used herein have the same meaning as commonly understood by one of skill in the art to which the invention pertains. Although any methods and materials similar herein can be used in the practice or testing of the present invention, the preferred methods and materials are described herein.

The following examples are offered by way of illustration and not by way of limitation.

EXPERIMENTAL

Example 1

*Bacillus thuringiensis* Culture and Endotoxin Sample Preparation

Strains of *Bacillus thuringiensis* were grown up according to the following protocol:
1. Prepare 96-well plates with 1 ml LB per well.
2. Move *Bacillus thuringiensis* glycerol stock plate from −80 C onto ice.
3. Inoculate LB plate with glycerol stock.
4. Grow LB plate at 30 C, 250 rpm for 18 hours.
5. Prepare 96-deep well plates with 1 ml CYS3 medium per well.
6. Inoculated CYS3 plates with 20 ul overnight Bt culture per well.
7. Grow CYS3 plates at 30 C, 300 rpm for 3 day.
8. Centrifuge CYS3 plates at 4 C, 4000 rpm for 40 min.
9. Discard pellets and resuspent pellet in 1 ml distilled water.
10. Centrifuge at 4 C, 4000 rpm for 40 min.
11. Discard supernatant and resuspent pellet in 0.5% lysozyme solution and incubate plates at 37 C, 250 rpm overnight.
12. Centrifuge at 4 C, 4000 rpm and discard the supernatant.
13. Wash the pellet twice with 0.5M NaCl, each wash is followed by a centrifugation.

14. Wash with distilled water twice, resuspend the final pellet in 500 ul distilled water and store the plate in 4 C fridge.

Example 2

Nematode Feeding Assay

The *Bacillus thuringiensis* strains were individually tested for nematicidal activity using a *C. elegans* feeding assay:
1. 5-30 μL, of suspension was added into assay wells in 96-well plates.
2. Each assay well contains 120 μL of liquid with ~50 L1 staged *C. elegans,* 30 μg/mL tetracycline, 30 μg/mL chloramphenicol, and S-medium. *E. coli* strain OP50 was used as a control.
3. 48 hours later, the assay plates were scored under a microscope by checking the worm's growth and development.

4. Strain MG3G12 totally inhibited worm development and all worms were arrested at the L1 stage, indicating that the MG3G121 strain exhibits nematicidal activity.

Example 3

Mass Spectrometry Analysis and Sequence Amplification

An MG3G12 suspension sample was digested with trypsin and analyzed using Mass spectrometry; the resulting data was used to search peptide fragment databases. Some peptides showed homology to sequence fragments from the Cry14Aa protein.

Based on the mass spectroscopy results, a PCR-based strategy was used to amplify the putative novel Bt crystal protein.

1. Genomic DNA was extracted from strain MG3G12.

2. PCR primers were designed to amplify crystal proteins having homology to Cry14Aa.

3. PCR amplification was performed and amplified DNA fragments were isolated from agarose gel and cloned.

4. Cloned DNA fragments were sequenced, and the ORF was translated to determine the encoded protein.

The resulting clone, designated RX008, encodes a crystal protein showing 92% homology to Cry14Aa protein.

Example 4

Subcloning of RX008 in *E. coli* and Bt

To confirm that the RX008 DNA fragment contains coding sequence responsible for the nematicidal activity, specific primers were designed to isolate fragments using high fidelity PCR. The PCR products were subcloned into pMaxy3188 vector and pMaxy3221 vector. The pMaxy3188 vector was transformed into *E. coli* XL-1 blue and pMaxy3221 vector was transformed into Bt strain G8. Empty vectors were also transformed as negative controls.

*E. coli* cells which contained pM3188-RX008 were grown overnight in LB plus antibiotics and gene expression was induced by IPTG at 37° C. at 225 rpm. Induced and non-induced culture were fed to *C. elegans*, as described above. Induced *E. coli* cells that contained an RX008 expression vector showed strong nematicidal activity, similar to the original MG3G12 strain. In contrast, the negative control cells showed no inhibitory activity, indicating that the RX008 gene is primarily or solely responsible for the *C. elegans* nematicidal activity exhibited by the MG3G12 strain.

Bt G8 transformed with pMaxy3221-RX008 was cultured in CYS3 for 3 days and the crude crystal protein sample was prepared as described above. In *C. elegans* feeding assays, this crude samples showed similar nematicidal activity as the original strain MG3G12. This also confirmed that RX008 is the primary or sole component responsible for the nematicidal activity of the MG3G12 strain.

RX008 protein was solubilized and purified from BtG8 strain expressing the RX008 construct. Purified RX008 protein was tested on *C. elegans* using serial dilutions. The assay results indicated that the IC (inhibition concentration) 50 is 5 ppm and IC90 is 10 ppm.

Example 5

Identification of Fragments Retaining Nematicidal Activity

Since plant parasitic nematodes have specialized feeding structure, stylets and feeding tubes, small nematicidal proteins would have advantage in nematode control. We truncated RX008 from both ends to assess the nematicidal activity of RX008 truncation variants. Primers were designed to make different truncation proteins (see Table 1, below). Bioassays indicate that truncated RX008-684 maintains the full activity. RX008-684 protein and DNA sequences (SEQ ID NOs: 3 and 4, respectively) are showed in FIG. 2.

TABLE 1

| Gene | Amino acids | Amino acid truncated from N-terminal | Amino acid truncated from C-terminal | Nematicidal activity on *C. elegans* |
|---|---|---|---|---|
| RX008 | 1188 | 0 | 0 | strong |
| RX008-750 | 750 | 0 | 438 | strong |
| RX008-684 | 684 | 0 | 504 | strong |
| RX008-672 | 672 | 0 | 516 | weak |
| RX008-640 | 640 | 0 | 548 | no |
| RX008-34 | 651 | 33 | 504 | no |
| RX008-24 | 661 | 23 | 504 | weak |

Example 6

δ-Endotoxin Variants

A. Polynucleotide Variants

The nucleotide sequence set forth in SEQ ID NO: 2 is used to generate variant nucleotide sequences having the nucleotide sequence of the open reading frame with about 70%, 76%, 81%, 86%, 92%, and 97% nucleotide sequence identity when compared to the starting unaltered ORF nucleotide sequence of SEQ ID NO: 2. These functional variants are generated using a standard codon table. While the nucleotide sequence of the variant is altered, the amino acid sequence encoded by the open reading frame does not change.

B. Variant Amino Acid Sequences

Variant amino acid sequences of SEQ ID NO: 1 are generated. In this example, one amino acid is altered. Specifically, the open reading frame set forth in SEQ ID NO: 2 is reviewed to determined the appropriate amino acid alteration. The selection of the amino acid to change is made by consulting a protein alignment (e.g., with Cry14A, Cry21A, and Cry 5B). An amino acid is selected that is deemed not to be under high selection pressure (not highly conserved) and which is rather easily substituted by an amino acid with similar chemical characteristics (i.e., similar functional side-chain). Using the protein alignment an appropriate amino acid can be changed.

Once the targeted amino acid is identified, the procedure outlined in Example 6A is followed. Variants having about 70%, 75%, 81%, 86%, 92%, and 97% nucleic acid sequence identity to SEQ ID NO: 2 are generated using this method.

C. Additional Amino Acid Sequence Variants

In this example, artificial protein sequences are created having 82%, 87%, 92%, and 97% identity relative to the reference protein sequence (SEQ ID NO: 1). This latter effort requires identifying conserved and variable regions and then the judicious application of an amino acid substitutions table. These parts will be discussed in more detail below.

The determination of which amino acid sequences are altered is made largely based on the conserved δ-endotoxin domains and the extent to which amino acid residues in those domains tend to be conserved between δ-endotoxins. Based on sequence alignments, the various regions of SEQ ID NO: 1 that can likely be altered are identified. Typically, conservative substitutions can be made in conserved domains (e.g., endotoxin N, M, and C domains) without altering function. In addition, one of skill will understand that functional variants of the polypeptides of the invention can have minor non-conserved amino acid alterations in the conserved domain. Positions more amenable to non-conserved amino acid alterations can be identified by modeling the structure of the δ-endotoxin domains and locating surface residues that are not conserved between functionally related δ-endotoxins (e.g., Cry14A, Cry21A, and Cry 5B).

The conserved domains of SEQ ID NO: 1 are found between about amino acid 64 to about amino acid 318 (endotoxin N domain), about amino acid 322 to about amino acid 526 (endotoxin M domain), and about amino acid 539 to about amino acid 684 (endotoxin C domain).

Artificial protein sequences are then created that are different from the original in the intervals of 80-85%, 85-90%, 90-95%, and 95-100% identity. Midpoints of these intervals are targeted, with liberal latitude of plus or minus 1%, for example. The amino acids substitutions will be effected by a custom Perl script. The substitution table is provided below in Table 2.

TABLE 2

Substitution Table

| Amino Acid | Strongly Similar and Optimal Substitution | Rank of Order to Change | Comment |
| --- | --- | --- | --- |
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

First, any conserved amino acids in the protein that should not be changed is identified and "marked off" for insulation from the substitution. The start methionine will of course be added to this list automatically. Next, the changes are made.

H, C, and P are not changed in any circumstance. The changes will occur with isoleucine first, sweeping N-terminal to C-terminal. Then leucine, and so on down the list until the desired target it reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involved a 50:50 substitution of the two alternate optimal substitutions.

The variant amino acid sequences are written as output. Perl script is used to calculate the percent identities. Using this procedure, variants are generating having about 82%, 87%, 92%, and 97% amino acid identity to the starting unaltered ORF nucleotide sequence of SEQ ID NO: 1.

Example 7

Transformation of Soybean Root Cultures and Testing of Soybean Cyst Nematode (SCN) Resistance

*Agrobacterium rhizogenes* strain K599 was used for soybean hairy root transformation, and the gene function and promoter activity were analyzed in transgenic soybean hairy roots. Stocks of *A. rhizogenes* were maintained on minimal A media (see recipes, below). Plasmid DNA was introduced into *A. rhizogenes* strain K599 using the freeze-thaw method, as described in Ha (1988) Plant Molecular Manual, eds. Gelvin, Schilperoort, and Verma, pp. A3/1-A3/7.

Soybean seeds were surface-sterilized with chlorine gas at room temperature for 12-16 hours. The seeds were then aerated in a clean air hood for at least 30 minutes. Seeds were germinated and cultured in Magenta™ boxes (Magenta Corporation) containing sterile potting soil with 10 to 15 mL of 25% Gamborg's B-5 Basal medium with minimal organics (G5893, Sigma). The boxes were placed under a mix of fluorescent and incandescent lights providing a 16-hour day/8-hour night cycle and constant temperature of about 26° C. Six-day-old seedlings of non-transformed plants were inoculated with a freshly grown culture of *A. rhizogenes* previously transformed with DNA constructs. The transformed *A. rhizogenes* was introduced into the hypocotyls just under the cotyledons by wounding 4 to 6 times in the epidermal cell layer with a 23-gauge needle containing the *A. rhizogenes*. The inoculated plants were cultured under the same conditions as those described above for seed germination.

After the soybean hypocotyls were inoculated with *A. rhizogenes*, adventitious soybean roots developed and were excised. Initially these putative transformed roots were cultured in liquid B-5 medium with antibiotics to cure the roots of any bacteria; antibiotics included 500 mg/L cefotaxime (Calbiochem-Novabiochem, La Jolla, Calif.) and 200 mg/L vancomycin (Spectrum Quality Products, Los Angeles, Calif.). Roots were transferred to fresh liquid medium every 2-3 days; this transfer to fresh media is performed a total of three times. After the third transfer, each root was moved to a plate of MXB medium with Gelrite™ gelling agent. To determine whether roots were transformed, a 1-2 cm root piece was placed in a 1.5 mL tube with GUS staining solution (0.05% X-Gluc in 100 mM sodium phosphate buffer at pH 7.0 containing 10 mM EDTA, 0.1% Triton, and 0.5 mM K4Fe(CN)-61420). Roots were incubated in this solution for 2 to 4 hours at 27 to 29° C.; solutions were then evaluated for development of the blue color indicative of GUS activity.

Roots testing positive by this assay and control roots that were not transformed were cultured in MXB medium with Gelrite™ gelling agent in an incubator without light at 26 to 30° C. A 1-4 cm piece of root tip was excised and transferred to fresh medium every 2-4 weeks.

Roots testing positive for transformation with the DNA construct were assayed for resistance to infection by soybean cyst nematodes (SCN). Roots were transferred to 6-well plates containing NM medium with Daishin agar. After 4-10 days, roots were inoculated with second-stage SCN juveniles. Two to five root tips were placed in each well of a 6-well culture dish; four of the wells contained roots transformed with *A. rhizogenes* containing the RX008 construct and the other two wells contained control roots transformed with *A. rhizogenes* lacking the RX008 construct. One sample of control roots in this assay was an SCN-compatible control root sample from an SCN-susceptible or "compatible" soybean genotype such as Pioneer brand 9204. The other sample of control roots was an SCN-resistant soybean genotype such as Jack and is thus an SCN-resistant or "incompatible" control sample. Roots were inoculated by placing 500 second-stage SCN race 3 juveniles directly onto the roots in each well and incubating for 7 days at 26 to 28° C.

The following stock solutions and media are used for transformation and regeneration of soybean roots:
Stock Solutions (Per Liter):
B-5 Majors: 25.00 g KNO3, 1.34 g (NH4)2SO4, 2.50 g MgSO4-7H2O, 1.50 g CaCl2-2H2O, 1.31 g NaH2PO4 (anhydrous).
B-5 Minors: 1.00 g MnSO4-H2O, 0.30 g H3BO3, 0.20 g ZnSO4-7H2O, 0.075 g KI.
B-5 Vitamin Stock with Thiamine: 1 L Vitamin B-5 Stock, 1 g Thiamine HCl.
Iron Mix: 3.73 g. Na2EDTA, 2.78 g FeSO4-7H2O.
Media (per Liter):
Minimal A medium: 10.5 g K2HPO4, 4.5 g KH2PO4, 1.0 g (NH4)2SO4, 0.5 g (Na)2C6HSO7-2H2O, 1 mL 1.0 M MgSO4-7H2O, 10 mL 20% w/v sucrose, 15 g agar,
B-5 medium: 0.6 g MES (2-(N-Morpholino) ethane-sulfonic acid (M5287, Sigma)), 20 g sucrose, 10 mL B-5 minors, 100 mL B-5 majors, 10 mL B-5 Vitamin Stock with Thiamine, 10 mL Iron mix.
MXB medium: Murashige and Skoog Basal nutrient salts (M5524, Sigma), 10 mL Vitamin B-5 Stock with Thiamine, 30 g sucrose.
MXB medium with Gelrite™: add 3 g Gelrite gelling agent to 1 L MXB medium, pH 5.7.
MXB medium with Daishin agar: add 8 g Daishin agar to 1 L MXB medium, pH 6.5.

Six weeks after SCN inoculation, the cyst numbers were counted from each plate and the data was analyzed. In these hairy root assays, expression of the RX008 construct resulted in a 22% reduction number of cysts, as compared to the empty vector control (see FIG. 4). For expression in soybean cells, the RX008 sequence was optimized based on soy codon usage and a BAA signal was add to the N-terminal of the gene. The BAA-RX008 construct (SEQ ID NO:6) was transformed into soybean hairy roots as described above.

Example 8

Transformation of Soybean Embryos

Culture Conditions
Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the following examples by the method of particle gun bombardment (Klein et al. (1987) *Nature,* 327:70).
Soybean Embryogenic Suspension Culture Initiation
Soybean cultures are initiated twice each month with 5-7 days between each initiation.

Pods with immature seeds from available soybean plants 45-55 days after planting are picked, removed from their shells and placed into a sterilized magenta box. The soybean seeds are sterilized by shaking them for 15 minutes in a 5% Clorox solution with 1 drop of ivory soap (95 ml of autoclaved distilled water plus 5 ml Clorox and 1 drop of soap). Mix well. Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.
Preparation of DNA for Bombardment
Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying a δ-endotoxin protein coding sequence are obtained by gel isolation of double digested plasmids. In each case, 100 ug of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing the δ-endotoxin protein coding sequence are cut from the agarose gel. DNA is purified from the agarose using the GELase digesting enzyme following the manufacturer's protocol.

A 50 µl aliquot of sterile distilled water containing 3 mg of gold particles (3 mg gold) is added to 5 µl of a 1 µg/µl DNA solution (either intact plasmid or DNA fragment prepared as described above), 50 µl 12.5M $CaCl_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS1000/HE instrument disk. Each 5 µl aliquot contains approximately 0.375 mg gold per bombardment (i.e. per disk).
Tissue Preparation and Bombardment with DNA
Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.
Selection of Transformed Embryos
Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for nematode and/or insect resistance.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for proteins.

Media Recipes

| SB 196 - FN Lite liquid proliferation medium (per liter) - | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| KNO3 | 2.83 gm |
| (NH4)2SO4 | 0.463 gm |
| Asparagine | 1.0 gm |
| Sucrose (1%) | 10 gm | pH 5.8

FN Lite Stock Solutions

| Stock # | | 1000 ml | 500 ml |
|---|---|---|---|
| 1 | MS Fe EDTA 100x Stock | | |
| | Na$_2$EDTA* | 3.724 g | 1.862 g |
| | FeSO$_4$—7H$_2$O | 2.784 g | 1.392 g |
| 2 | MS Sulfate 100x stock | | |
| | MgSO$_4$—7H$_2$O | 37.0 g | 18.5 g |
| | MnSO$_4$—H$_2$O | 1.69 g | 0.845 g |
| | ZnSO$_4$—7H$_2$O | 0.86 g | 0.43 g |
| | CuSO$_4$—5H$_2$O | 0.0025 g | 0.00125 g |
| 3 | FN Lite Halides 100x Stock | | |
| | CaCl$_2$—2H$_2$O | 30.0 g | 15.0 g |
| | KI | 0.083 g | 0.0715 g |
| | CoCl$_2$—6H$_2$O | 0.0025 g | 0.00125 g |
| 4 | FN Lite P, B, Mo 100x Stock | | |
| | KH$_2$PO$_4$ | 18.5 g | 9.25 g |
| | H$_3$BO$_3$ | 0.62 g | 0.31 g |
| | Na$_2$MoO$_4$—2H$_2$O | 0.025 g | 0.0125 g |

*Add first, dissolve in dark bottle while stirring

SB1 solid medium (per liter) comprises: 1 pkg. MS salts (Gibco/BRL-Cat#11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (Gibco/BRL-Cat#11117-066); 1 ml B5 vitamins 1000× stock; 60 g maltose; 750 mg MgC12 hexahydrate; 5 g activated charcoal; pH 5.7; and, 2 g gelrite.

SB 103 solid medium (per liter) comprises: 1 pkg. MS salts (Gibco/BRL-Cat#11117-066); 1 ml B5 vitamins 1000× stock; 60 g maltose; 750 mg MgC12 hexahydrate; pH 5.7; and, 2 g gelrite.

SB 71-4 solid medium (per liter) comprises: 1 bottle Gamborg's B5 salts w/sucrose (Gibco/BRL-Cat#21153-036); pH 5.7; and, 5 g TC agar.

2,4-D stock is obtained premade from Phytotech cat# D 295—concentration is 1 mg/ml.

B5 Vitamins Stock (per 100 ml) which is stored in aliquots at −20 C comprises: 10 g myo-inositol; 100 mg nicotinic acid; 100 mg pyridoxine HCl; and, 1 g thiamine. If the solution does not dissolve quickly enough, apply a low level of heat via the hot stir plate. Chlorsulfuron Stock comprises 1 mg/ml in 0.01 N Ammonium Hydroxide.

Example 9

Transformation and Regeneration of Transgenic Maize Plants

Immature maize embryos from greenhouse donor plants are bombarded with a plasmid containing a nucleotide sequence encoding a δ-endotoxin polypeptide of the invention (SEQ ID NO: 1) operably linked to a promoter that drives expression in a maize plant cell and a selectable marker (e.g., the selectable marker gene PAT (Wohlleben et al. (1988) *Gene* 70:25-37), which confers resistance to the herbicide Bialaphos). Alternatively, the selectable marker gene is provided on a separate plasmid.

Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a nucleotide sequence encoding a δ-endotoxin polypeptide of the invention operably linked to a promoter that drives expression in a maize cell is made. This plasmid DNA, plus plasmid DNA containing a selectable marker (e.g., PAT), is precipitated onto 1.1 μm (average diameter) tungsten pellets using a $CaCl_2$ precipitation procedure as follows:

100 μL prepared tungsten particles in water
10 μL (1 μg) DNA in Tris EDTA buffer (1 μg total DNA)
100 μL 2.5 M $CaCl_2$
10 μL 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 μL 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

Particle Gun Treatment

The sample plates are bombarded at level #4 in a particle gun. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/L Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for nematode and/or insect resistance.

Bombardment and Culture Media

Bombardment medium (560Y) comprises 4.0 g/L N6 basal salts (SIGMA C-1416), 1.0 mL/L Eriksson's Vitamin Mix (1000× SIGMA-1511), 0.5 mg/L thiamine HCl, 120.0 g/L sucrose, 1.0 mg/L 2,4-D, and 2.88 g/L L-proline (brought to volume with D-I $H_2O$ following adjustment to pH 5.8 with KOH); 2.0 g/L Gelrite (added after bringing to volume with D-I $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000× SIGMA-1511), 0.5 mg/L thiamine HCl, 30.0 g/L sucrose, and 2.0 mg/L 2,4-D (brought to volume with D-I $H_2O$ following adjustment to pH 5.8 with KOH); 3.0 g/L Gelrite (added after bringing to volume with D-I $H_2O$); and 0.85 mg/L silver nitrate and 3.0 mg/L bialaphos (both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCL, 0.10 g/L pyridoxine HCL, and 0.40 g/L glycine brought to volume with polished D-I $H_2O$) (Murashige and Skoog (1962) *Physiol. Plant.* 15:473), 100 mg/L myo-inositol, 0.5 mg/L zeatin, 60 g/L sucrose, and 1.0 mL/L of 0.1 mM abscisic acid (brought to volume with polished D-I $H_2O$ after adjusting to pH 5.6); 3.0 g/L Gelrite (added after bringing to volume with D-I $H_2O$); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCL, 0.10 g/L pyridoxine HCL, and 0.40 g/L glycine brought to volume with polished D-I $H_2O$), 0.1 g/L myo-inositol, and 40.0 g/L sucrose (brought to volume with polished D-I $H_2O$ after adjusting pH to 5.6); and 6 g/L bacto-agar (added after bringing to volume with polished D-I $H_2O$), sterilized and cooled to 60° C.

Example 10

*Agrobacterium*-Mediated Transformation of Maize and Regeneration of Transgenic Plants For *Agrobacterium*-mediated transformation of maize with a nucleotide sequence encoding a δ-endotoxin polypeptide of the invention, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the polynucleotide construct to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is performed. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the foregoing list of embodiments and appended claims. Although specific terms are employed herein, they are used in a generic and descriptive sense only and not for purposes of limitation.

That which is claimed:

1. An expression cassette comprising a heterologous promoter operably linked to a polynucleotide comprising a nucleotide sequence selected from the group consisting of:
   (a) a nucleotide sequence comprising SEQ ID NO: 2;
   (b) a nucleotide sequence encoding a polypeptide comprising the amino acid sequence of SEQ ID NO: 1; and
   (c) a nucleotide sequence encoding a polypeptide comprising residues 23-684 of SEQ ID NO: 1, wherein said amino acid sequence has nematicidal activity.

2. The expression cassette of claim 1, wherein said polynucleotide is operably linked to a promoter that drives expression in a plant.

3. The expression cassette of claim 1, wherein said polynucleotide is operably linked to a promoter that drives expression in a microorganism.

4. A plant comprising a heterologous polynucleotide operably linked to a promoter that drives expression in the plant, wherein said heterologous polynucleotide comprises a nucleotide sequence selected from the group consisting of:
   (a) a nucleotide sequence comprising SEQ ID NO: 2;
   (b) a nucleotide sequence encoding a polypeptide comprising the amino acid sequence of SEQ ID NO: 1; and
   (c) a nucleotide sequence encoding a polypeptide comprising residues 23-684 of SEQ ID NO: 1, wherein said amino acid sequence has nematicidal activity.

5. A seed of the plant of claim 4, wherein said seed comprises said heterologous polynucleotide.

6. A microorganism comprising at least one heterologous polynucleotide operably linked to a promoter that drives expression in the microorganism, wherein said heterologous polynucleotide comprises a nucleotide sequence selected from the group consisting of:
   (a) a nucleotide sequence comprising SEQ ID NO: 2;
   (b) a nucleotide sequence encoding a polypeptide comprising the amino acid sequence of SEQ ID NO: 1; and
   (c) a nucleotide sequence encoding a polypeptide comprising residues 23-684 of SEQ ID NO: 1, wherein said amino acid sequence has nematicidal activity.

7. A biopesticide composition comprising at least one microorganism according to claim 6.

8. The biopesticide composition of claim 7, further comprising a carrier.

9. The expression cassette of claim 1, wherein said polynucleotide encodes a polypeptide that binds to a glycolipid comprising the tetrasaccharide sequence N-acetylgalactosamine β1-4 N-acetylglucosamine β1-3 mannose β1-4 glucose and facilitates the formation of a pore in an invertebrate cellular membrane containing said glycolipid.

10. The expression cassette of claim 1, wherein said polynucleotide encodes a polypeptide having nematicidal activity against a nematode that is a member of a *Meloidogyne*, *Heterodera*, or *Globedera* genera, or a nematode selected from the group consisting of *Panagrellus redivivus, Distolabrellus veechi, Nippostrongylus brasiliensis*, and *Caenorhabditis elegans*.

* * * * *

```
                        SEQUENCE LISTING

<160> NUMBER OF SEQ ID NOS: 6

<210> SEQ ID NO 1
<211> LENGTH: 1187
<212> TYPE: PRT
<213> ORGANISM: Bacillus thuringiensis

<400> SEQUENCE: 1

Met Arg Met Asp Cys Asn Leu Gln Ser Gln Gln Asn Ile Pro Tyr Asn
 1               5                  10                  15

Val Leu Ala Ile Pro Val Ser Asn Val Asn Ala Leu Val Asp Thr Ala
             20                  25                  30

Lys Asp Leu Lys Glu Ala Trp Glu Ala Phe Gln Lys Thr Gly Ser Phe
         35                  40                  45

Ser Leu Thr Ala Leu Gln Gln Gly Phe Ser Ala Ser Gln Gly Gly Ala
     50                  55                  60

Phe Asn Tyr Leu Thr Leu Leu Gln Ser Gly Ile Ser Leu Ala Gly Ser
 65                  70                  75                  80

Phe Val Pro Gly Gly Thr Phe Val Ala Pro Ile Val Asn Met Val Ile
                 85                  90                  95

Gly Trp Leu Trp Pro His Lys Asn Lys Thr Ala Asp Thr Glu Asn Leu
            100                 105                 110

Ile Lys Leu Ile Asp Glu Glu Ile Gln Lys Gln Leu Asn Lys Ala Leu
        115                 120                 125

Leu Glu Gln Asp Lys Asn Asn Trp Thr Ser Phe Leu Glu Ser Ile Phe
    130                 135                 140

Asp Val Ser Asn Thr Val Ser Asn Ala Met Ile Asp Ala Gln Trp Ser
145                 150                 155                 160

Gly Thr Val Asp Thr Thr Asn Arg Gln Pro Lys Thr Pro Thr Thr Ser
                165                 170                 175

Asp Tyr Leu Asn Val Val Gly Lys Phe Asp Ser Ala Asp Ser Ala Ile
            180                 185                 190

Val Thr Asn Glu Asn Gln Ile Met Asn Gly Asn Phe Asp Val Ala Ala
        195                 200                 205

Ser Pro Tyr Phe Val Ile Gly Ala Thr Leu Arg Leu Ser Leu Phe Gln
    210                 215                 220

Ser Tyr Ile Lys Phe Cys Asn Asn Trp Ile Asp Ala Val Gly Phe Asn
225                 230                 235                 240

Pro Ser Asp Ser Asn Thr Gln Lys Ala Asn Leu Ala Arg Met Lys Gln
                245                 250                 255

Thr Met Arg Ile Thr Ile Asn Glu Tyr Thr Gln Arg Ile Met Lys Val
            260                 265                 270

Phe Lys Asp Pro Lys Asn Met Pro Thr Ile Gly Thr Asn Lys Phe Ser
        275                 280                 285

Val Asp Ala Tyr Asn Val Tyr Val Lys Gly Met Thr Leu Asn Val Leu
    290                 295                 300

Asp Met Val Ala Ile Trp Pro Ser Leu Tyr Pro Asn Asp Tyr Thr Ser
```

```
            305                 310                 315                 320
Gln Thr Thr Leu Glu Gln Thr Arg Val Thr Phe Ser Asn Met Val Gly
                325                 330                 335

Gln Glu Glu Gly Thr Asp Gly Thr Leu Lys Ile Tyr Asn Thr Phe Asp
                340                 345                 350

Ser Ser Ser Phe Gln His Ser Leu Ile Pro Asn Asn Val Asp Leu
                355                 360                 365

Ile Ser Tyr Phe Asn Asp Glu Leu Gln Asn Leu Glu Leu Ala Val Tyr
                370                 375                 380

Thr Pro Pro Lys Lys Asp Ser Gly Tyr Ser Tyr Pro Tyr Gly Phe Val
385                 390                 395                 400

Leu Lys Tyr Ala Asn Ser Lys Tyr Lys Tyr Gly Asp Ser Asn Asp Pro
                405                 410                 415

Glu Ser Leu Gly Gly Leu Ser Thr Leu Ser Ala Pro Ile Gln Gln Ile
                420                 425                 430

Asn Ala Ala Thr Gln Asn Ser Lys Tyr Leu Asp Gly Glu Thr Ile Asn
                435                 440                 445

Gly Ile Gly Ala Ser Leu Pro Gly Tyr Cys Thr Thr Gly Cys Ser Ala
                450                 455                 460

Thr Glu Gln Pro Phe Ser Cys Thr Ser Asn Ala Asn Ser Tyr Lys Ser
465                 470                 475                 480

Ser Cys Asn Pro Ser Asp Thr Asn Gln Lys Ile Asn Ala Leu Tyr Ala
                485                 490                 495

Phe Thr Gln Thr Asn Val Lys Gly Asn Thr Gly Lys Leu Gly Val Leu
                500                 505                 510

Ala Ser Leu Val Pro Tyr Asp Leu Asn Pro Lys Asn Val Phe Gly Glu
                515                 520                 525

Leu Asp Ser Asp Thr Asn Val Ile Leu Lys Gly Ile Pro Ala Glu
                530                 535                 540

Lys Gly Tyr Phe Ser Asn Asn Ala Arg Pro Thr Val Val Lys Glu Trp
545                 550                 555                 560

Ile Asn Gly Ala Ser Ala Val Pro Leu Tyr Ser Gly Asn Thr Leu Phe
                565                 570                 575

Met Thr Ala Thr Asn Leu Thr Ala Thr Gln Tyr Lys Ile Arg Ile Arg
                580                 585                 590

Tyr Ala Asn Pro Asn Ser Asp Thr Gln Ile Gly Val Arg Ile Thr Gln
                595                 600                 605

Asn Gly Ser Leu Ile Ser Asn Ser Asn Pro Leu Tyr Ser Thr Thr
                610                 615                 620

Asp Ser Ser Met Ser Ser Asn Leu Pro Gln Asn Val Tyr Val Thr Gly
625                 630                 635                 640

Glu Asn Gly Asn Tyr Thr Leu Leu Asp Leu Tyr Ser Thr Asn Asn Val
                645                 650                 655

Leu Ser Thr Gly Asp Ile Thr Leu Gln Leu Thr Gly Gly Asn Gln Lys
                660                 665                 670

Ile Phe Ile Asp Arg Ile Glu Phe Ile Pro Thr Met Pro Val Pro Ala
                675                 680                 685

Ala Thr Asn Asn Asn Asn Gly Asp Asn Asp Pro Pro Ile His His
                690                 695                 700

Gly Cys Ala Ile Ala Gly Thr Gln Gln Leu Cys Ala Gly Pro Pro Lys
705                 710                 715                 720

Phe Glu Gln Val Ser Asp Leu Glu Lys Ile Thr Thr Gln Val Tyr Met
                725                 730                 735
```

-continued

```
Leu Phe Lys Ser Ser Leu Tyr Glu Glu Leu Asp Pro Lys Val Ser Ser
            740                 745                 750

Tyr Gln Ile Asn Gln Val Ala Leu Lys Val Met Ala Leu Ser Asn Glu
            755                 760                 765

Lys Phe Cys Glu Glu Lys Arg Leu Leu Arg Lys Leu Val Asn Lys Ala
            770                 775             780

Asn Gln Leu Leu Glu Ala Arg Asn Leu Val Gly Gly Asn Phe Glu
785             790                 795                 800

Thr Thr Gln Asn Trp Val Leu Gly Thr Asn Ala Tyr Ile Asn Tyr Asp
                    805                 810                 815

Ser Phe Leu Phe Asn Gly Asn Tyr Leu Ser Leu Gln Pro Ala Ser Gly
            820                 825                 830

Phe Phe Thr Ser Tyr Ala Tyr Gln Lys Ile Asp Glu Ser Thr Leu Lys
                835                 840                 845

Pro Tyr Thr Arg Tyr Lys Val Ser Gly Phe Ile Gly Gln Ser Asn Gln
            850                 855                 860

Val Glu Leu Ile Ile Ser Arg Tyr Gly Lys Glu Ile Asp Lys Ile Leu
865                 870                 875                 880

Asn Val Pro Tyr Ala Gly Pro Leu Pro Ile Thr Ala Asp Ala Ser Ile
                    885                 890                 895

Thr Cys Cys Ala Pro Glu Ile Asp Gln Cys Asp Gly Gly Gln Ser Asp
                900                 905                 910

Ser His Phe Phe Asn Tyr Ser Ile Asp Val Gly Ala Leu His Pro Glu
            915                 920                 925

Leu Asn Pro Gly Ile Glu Ile Gly Leu Lys Ile Val Gln Ser Asn Gly
        930                 935                 940

Asn Ile Thr Ile Ser Asn Leu Glu Ile Ile Glu Glu Arg Pro Leu Thr
945                 950                 955                 960

Glu Met Glu Ile Gln Thr Val Asn Arg Lys Asp Gln Lys Trp Lys Arg
                    965                 970                 975

Glu Lys Leu Leu Glu Cys Ala Ser Ile Ser Glu Leu Leu Gln Pro Ile
                980                 985                 990

Ile Asn Gln Ile Asp Ser Leu Phe Lys Asp Ala Asn Trp Tyr Asn Asp
            995                 1000                1005

Ile Leu Pro His Val Thr Tyr Gln Thr Leu Lys Asn Ile Ile Val Pro
    1010                1015                1020

Asp Leu Pro Lys Leu Lys His Trp Phe Ile Asp Leu Pro Gly Glu
1025                1030                1035                1040

Tyr Tyr Glu Ile Glu Gln Lys Met Lys Glu Ala Leu Lys His Ala Phe
                1045                1050                1055

Thr Gln Leu Asp Glu Lys Asn Leu Ile Tyr Asn Gly Asp Phe Thr Thr
            1060                1065                1070

Asn Leu Ile Asp Trp Gln Ile Glu Gly Asp Ala Arg Met Lys Val Leu
            1075                1080                1085

Glu Asn Asn Ala Leu Ala Leu Gln Leu Ser Asn Trp Asp Ser Ser Val
            1090                1095                1100

Ser Gln Ser Ile Asp Ile Leu Glu Phe Asp Glu Asp Lys Ala Tyr Lys
1105                1110                1115                1120

Leu Arg Val Tyr Ala Gln Gly Ser Gly Thr Ile Gln Phe Gly Asn Cys
            1125                1130                1135

Glu Asp Glu Ala Ile Gln Phe Asn Thr Asn Ser Phe Val Tyr Lys Glu
            1140                1145                1150
```

Lys Ile Ile Tyr Phe Asp Thr Pro Ser Ile Asn Leu His Ile Gln Ser
              1155                 1160                 1165

Glu Gly Pro Glu Phe Val Val Ser Ser Ile Asp Leu Val Glu Leu Ser
         1170                 1175                 1180

Asp Asp Glu
1185

<210> SEQ ID NO 2
<211> LENGTH: 3564
<212> TYPE: DNA
<213> ORGANISM: Bacillus thuringiensis

<400> SEQUENCE: 2

| | | | | | | |
|---|---|---|---|---|---|---|
| atgcgaatgg | attgtaattt | acaatcacaa | caaatatttc | cttataatgt | attagcaata | 60 |
| ccagtatcta | atgttaatgc | gttggttgat | acagctaaag | atttaaaaga | agcatgggaa | 120 |
| gcatttcaaa | aaactggttc | ttttttcatta | acagctttac | aacaaggatt | ttctgcctca | 180 |
| caaggaggag | cattcaatta | tttaacatta | ttacaatcag | gaatatcatt | agctggttct | 240 |
| tttgtccctg | gaggtacttt | tgtagcaccc | attgttaata | tggttattgg | ttggttatgg | 300 |
| ccacataaaa | acaagacagc | ggatacgaaa | aatttaataa | aattaattga | tgaagaaatt | 360 |
| caaaaacaat | taaacaaagc | cttattagag | caagataaaa | acaattggac | ctctttttta | 420 |
| gaaagtatat | ttgatgtttc | aaatacagta | agtaatgcaa | tgatagatgc | tcagtggtca | 480 |
| ggtactgtag | atactacaaa | tagacaacca | aaaactccaa | caacatcaga | ttatctaaat | 540 |
| gttgttggaa | aatttgattc | agcggattct | gcaattgtaa | ctaatgaaaa | tcaaataatg | 600 |
| aacggcaact | ttgacgtagc | tgcatcaccc | tattttgtta | taggagcaac | attacgtctt | 660 |
| tcattatttc | aatcttatat | taaattttgt | aataattgga | ttgatgcagt | tggatttaat | 720 |
| ccatcagatt | ctaatacaca | aaaggctaat | ttagctcgta | tgaaacaaac | tatgcgtatt | 780 |
| acaattaacg | agtatacaca | agaattatg | aaagttttta | aagatcccaa | gaatatgcct | 840 |
| acaataggta | ctaataaatt | tagtgttgat | gcttataatg | tatatgttaa | aggaatgaca | 900 |
| ttaaatgttt | tagatatggt | agcaaatatg | ccttcattat | atccaaatga | ttatacttca | 960 |
| caaacaacct | tagaacaaac | acgtgtcact | ttttcaaata | tggttggtca | agaagaaggt | 1020 |
| acagatggaa | ccctaaaaat | ttacaatact | tttgattcta | gtagttttca | acatagccta | 1080 |
| atacctaata | taatgttga | tttaatttct | tattttaatg | atgaattgca | aaatttagaa | 1140 |
| ttagcagtat | ataccctcc | taaaaaggat | agtggatata | gttatcctta | tggatttgtt | 1200 |
| ttaaaatatg | caaacagtaa | atataaatat | ggtgatagca | atgatccaga | atctttagga | 1260 |
| ggattatcca | cactatctgc | acctatacaa | caaataaatg | cagcaactca | aacagtaaa | 1320 |
| tatctagatg | gagaaacaat | aaatggaata | ggggcgtcct | tacctggtta | ttgtactaca | 1380 |
| ggatgttcag | caacagaaca | acctttttagt | tgtacttcta | atgctaatag | ctataaatca | 1440 |
| agctgtaatc | cttcagatac | taatcaaaaa | attaatgctt | tatatgcttt | tacacaaact | 1500 |
| aatgtaaagg | gaaacacggg | gaaattagga | gtactggcaa | gtcttgttcc | atatgattta | 1560 |
| aatcctaaaa | atgtatttgg | tgaattagat | tcagatacaa | ataatgttat | cttaaaagga | 1620 |
| attcctgcag | aaaaagggta | ttttttctaat | aatgcgcgac | ctactgttgt | aaaagaatgg | 1680 |
| attaatggtg | caagtgctgt | accacttttat | tcaggaaata | cttttattat | gacggctacg | 1740 |
| aatttaacag | ctactcaata | taaattaga | atacgttatg | caaatccaaa | ttcagatact | 1800 |
| caaatcggtg | tacgaattac | gcaaaatggt | tctctaattt | ccaatagtaa | tccaccgctt | 1860 |

-continued

| | |
|---|---|
| tatagtacta ctgattcaag tatgagtagt aatttaccac aaaatgtata tgtcacaggg | 1920 |
| gaaaatggaa attatacact tctagattta tatagtacta ataatgtttt atcaacagga | 1980 |
| gatattacat tacaacttac aggaggaaat caaaaaatat ttattgatcg aatagaattt | 2040 |
| atacctacta tgcctgtacc tgctgctact aacaacaata acggcgataa cgatccccca | 2100 |
| ccgatacacc acggttgtgc aatagctggt acacaacaac tttgtgctgg accacctaag | 2160 |
| tttgaacaag taagtgattt agaaaaaatt acaacgcaag tatatatgtt attcaaatct | 2220 |
| tctttgtatg aagaattaga tccaaaagtt tccagctatc aaattaatca agtagcattg | 2280 |
| aaagttatgg cactatctaa tgaaagtttt tgtgaagaaa aaagattgtt acgaaaatta | 2340 |
| gtcaataaag caaccaatt actagaagca cgtaacttac tagtaggtgg aaattttgaa | 2400 |
| acaactcaaa attgggtact tggaacaaat gcttatataa attatgattc gttttttattt | 2460 |
| aatggaaatt atttatcctt acaaccagca agtggatttt tcacatctta tgcttatcaa | 2520 |
| aaaatagatg agtcaacatt aaaaccctat acacgtata aagtttctgg attcattggg | 2580 |
| caaagtaatc aagtagaact tattatttct cgttatggaa aagaaattga taaaatatta | 2640 |
| aatgttccat atgcagggcc tcttcctatt actgctgatg catcgataac ttgttgtgca | 2700 |
| ccagaaatag accaatgtga tgggggggcaa tctgattctc atttcttcaa ctatagcatc | 2760 |
| gatgtaggtg cacttcaccc agaattaaac cctggcattg aaattggtct taaaattgtg | 2820 |
| caatcaaatg gtaatataac aattagtaat ctagaaatta ttgaagaacg tccacttaca | 2880 |
| gaaatggaaa ttcaaacagt caatcgaaaa gatcaaaaat ggaaaagaga aaaacttcta | 2940 |
| gaatgtgcaa gtattagtga acttttacaa ccaatcatta atcaaatcga ttcattgttc | 3000 |
| aaagatgcaa actggtataa tgatattctt cctcatgtca catatcaaac tctaaaaaat | 3060 |
| attatagtac ccgatttacc aaaattaaaa cattggttca tagtgatct cccaggtgaa | 3120 |
| tattatgaaa ttgaacaaaa aatgaaagaa gctctaaaac atgcatttac acaattagac | 3180 |
| gagaaaaatt taatctacaa tggtgacttt acaactaact aatagattg gcaaatagaa | 3240 |
| ggtgatgctc gaatgaaagt attagaaaat aatgctttgg cattacaact ttccaattgg | 3300 |
| gattctagtg tttcacaatc tattgatata ttagaatttg atgaagataa agcatataaa | 3360 |
| cttcgcgtat atgctcaagg aagcggaaca atccaatttg gaaactgtga agatgaagcc | 3420 |
| atccaattta atacaaactc attcgtatat aaagaaaaaa taatatattt cgataccccca | 3480 |
| tcaattaact tacacataca atcagaaggt cctgaattcg ttgtaagtag tatcgacctc | 3540 |
| gttgaattat cagacgacga ataa | 3564 |

<210> SEQ ID NO 3
<211> LENGTH: 684
<212> TYPE: PRT
<213> ORGANISM: Artificial Sequence
<220> FEATURE:
<223> OTHER INFORMATION: Amino acid coding sequence for an active
      C-terminal truncation variant of RX008 from
      Bacillus thuringiensis.

<400> SEQUENCE: 3

Met Arg Met Asp Cys Asn Leu Gln Ser Gln Gln Asn Ile Pro Tyr Asn
1               5                   10                  15

Val Leu Ala Ile Pro Val Ser Asn Val Asn Ala Leu Val Asp Thr Ala
            20                  25                  30

Lys Asp Leu Lys Glu Ala Trp Glu Ala Phe Gln Lys Thr Gly Ser Phe
        35                  40                  45

```
Ser Leu Thr Ala Leu Gln Gln Gly Phe Ser Ala Ser Gln Gly Gly Ala
 50                  55                  60

Phe Asn Tyr Leu Thr Leu Leu Gln Ser Gly Ile Ser Leu Ala Gly Ser
 65                  70                  75                  80

Phe Val Pro Gly Gly Thr Phe Val Ala Pro Ile Val Asn Met Val Ile
                 85                  90                  95

Gly Trp Leu Trp Pro His Lys Asn Lys Thr Ala Asp Thr Glu Asn Leu
                100                 105                 110

Ile Lys Leu Ile Asp Glu Glu Ile Gln Lys Gln Leu Asn Lys Ala Leu
            115                 120                 125

Leu Glu Gln Asp Lys Asn Asn Trp Thr Ser Phe Leu Glu Ser Ile Phe
130                 135                 140

Asp Val Ser Asn Thr Val Ser Asn Ala Met Ile Asp Ala Gln Trp Ser
145                 150                 155                 160

Gly Thr Val Asp Thr Thr Asn Arg Gln Pro Lys Thr Pro Thr Thr Ser
                165                 170                 175

Asp Tyr Leu Asn Val Val Gly Lys Phe Asp Ser Ala Asp Ser Ala Ile
                180                 185                 190

Val Thr Asn Glu Asn Gln Ile Met Asn Gly Asn Phe Asp Val Ala Ala
            195                 200                 205

Ser Pro Tyr Phe Val Ile Gly Ala Thr Leu Arg Leu Ser Leu Phe Gln
210                 215                 220

Ser Tyr Ile Lys Phe Cys Asn Asn Trp Ile Asp Ala Val Gly Phe Asn
225                 230                 235                 240

Pro Ser Asp Ser Asn Thr Gln Lys Ala Asn Leu Ala Arg Met Lys Gln
                245                 250                 255

Thr Met Arg Ile Thr Ile Asn Glu Tyr Thr Gln Arg Ile Met Lys Val
                260                 265                 270

Phe Lys Asp Pro Lys Asn Met Pro Thr Ile Gly Thr Asn Lys Phe Ser
            275                 280                 285

Val Asp Ala Tyr Asn Val Tyr Val Lys Gly Met Thr Leu Asn Val Leu
290                 295                 300

Asp Met Val Ala Ile Trp Pro Ser Leu Tyr Pro Asn Asp Tyr Thr Ser
305                 310                 315                 320

Gln Thr Thr Leu Glu Gln Thr Arg Val Thr Phe Ser Asn Met Val Gly
                325                 330                 335

Gln Glu Glu Gly Thr Asp Gly Thr Leu Lys Ile Tyr Asn Thr Phe Asp
                340                 345                 350

Ser Ser Ser Phe Gln His Ser Leu Ile Pro Asn Asn Val Asp Leu
            355                 360                 365

Ile Ser Tyr Phe Asn Asp Glu Leu Gln Asn Leu Glu Leu Ala Val Tyr
            370                 375                 380

Thr Pro Pro Lys Lys Asp Ser Gly Tyr Ser Tyr Pro Tyr Gly Phe Val
385                 390                 395                 400

Leu Lys Tyr Ala Asn Ser Lys Tyr Lys Tyr Gly Asp Ser Asn Asp Pro
                405                 410                 415

Glu Ser Leu Gly Gly Leu Ser Thr Leu Ser Ala Pro Ile Gln Gln Ile
            420                 425                 430

Asn Ala Ala Thr Gln Asn Ser Lys Tyr Leu Asp Gly Thr Ile Asn
                435                 440                 445

Gly Ile Gly Ala Ser Leu Pro Gly Tyr Cys Thr Thr Gly Cys Ser Ala
450                 455                 460

Thr Glu Gln Pro Phe Ser Cys Thr Ser Asn Ala Asn Ser Tyr Lys Ser
```

```
                465                 470                 475                 480
Ser Cys Asn Pro Ser Asp Thr Asn Gln Lys Ile Asn Ala Leu Tyr Ala
                    485                 490                 495
Phe Thr Gln Thr Asn Val Lys Gly Asn Thr Gly Lys Leu Gly Val Leu
                500                 505                 510
Ala Ser Leu Val Pro Tyr Asp Leu Asn Pro Lys Asn Val Phe Gly Glu
                515                 520                 525
Leu Asp Ser Asp Thr Asn Asn Val Ile Leu Lys Gly Ile Pro Ala Glu
530                 535                 540
Lys Gly Tyr Phe Ser Asn Asn Ala Arg Pro Thr Val Val Lys Glu Trp
545                 550                 555                 560
Ile Asn Gly Ala Ser Ala Val Pro Leu Tyr Ser Gly Asn Thr Leu Phe
                565                 570                 575
Met Thr Ala Thr Asn Leu Thr Ala Thr Gln Tyr Lys Ile Arg Ile Arg
                580                 585                 590
Tyr Ala Asn Pro Asn Ser Asp Thr Gln Ile Gly Val Arg Ile Thr Gln
                595                 600                 605
Asn Gly Ser Leu Ile Ser Asn Ser Asn Pro Pro Leu Tyr Ser Thr Thr
                610                 615                 620
Asp Ser Ser Met Ser Ser Asn Leu Pro Gln Asn Val Tyr Val Thr Gly
625                 630                 635                 640
Glu Asn Gly Asn Tyr Thr Leu Leu Asp Leu Tyr Ser Thr Asn Asn Val
                645                 650                 655
Leu Ser Thr Gly Asp Ile Thr Leu Gln Leu Thr Gly Gly Asn Gln Lys
                660                 665                 670
Ile Phe Ile Asp Arg Ile Glu Phe Ile Pro Thr Met
                675                 680
```

```
<210> SEQ ID NO 4
<211> LENGTH: 2052
<212> TYPE: DNA
<213> ORGANISM: Artificial Sequence
<220> FEATURE:
<223> OTHER INFORMATION: Nucleic acid coding sequence for an active
      C-terminal truncation variant of RX008 from
      Bacillus thuringiensis.

<400> SEQUENCE: 4
atgcgaatgg attgtaattt acaatcacaa caaatatatc cttataatgt attagcaata       60
ccagtatcta atgttaatgc gttggttgat acagctaaag atttaaaaga agcatgggaa      120
gcatttcaaa aactggttc ttttttcatta acagctttac aacaaggatt ttctgcctca      180
caaggaggag cattcaatta tttaacatta ttacaatcag aatatccatt agctggttct      240
tttgtccctg gaggtactt tgtagcaccc attgttaata tggttattgg ttggttatgg      300
ccacataaaa acaagacagc ggatacagaa aatttaataa aattaattga tgaagaaatt      360
caaaaacaat taacaaagc cttattagag caagataaaa acaattggac ctcttttta       420 gaaagtatat ttgatgtttc aaatacagta agtaatgcaa tgatagatgc tcagtggtca      480
ggtactgtag atactacaaa tagacaacca aaaactccaa caacatcaga ttatctaaat      540
gttgttggaa aatttgattc agcggattct gcaattgtaa ctaatgaaaa tcaaataatg      600
aacggcaact tgacgtagc tgcatcaccc tattttgtta taggagcaac attacgtctt      660
tcattatttc aatcttatat taaatttgt aataattgga ttgatgcagt tggatttaat      720
ccatcagatt ctaatacaca aaaggctaat ttagctcgta tgaacaaac tatgcgtatt      780
```

```
acaattaacg agtatacaca aagaattatg aaagttttta aagatcccaa gaatatgcct      840
acaataggta ctaataaatt tagtgttgat gcttataatg tatatgttaa aggaatgaca      900
ttaaatgttt tagatatggt agcaatatgg ccttcattat atccaaatga ttatacttca      960
caaacaacct tagaacaaac acgtgtcact ttttcaaata tggttggtca agaagaaggt     1020
acagatggaa ccctaaaaat ttacaatact tttgattcta gtagttttca acatagccta     1080
atacctaata ataatgttga tttaatttct tattttaatg atgaattgca aaatttagaa     1140
ttagcagtat ataccccctcc taaaaaggat agtggatata gttatcctta tggatttgtt     1200
ttaaaatatg caaacagtaa atataaatat ggtgatagca atgatccaga atctttagga     1260
ggattatcca cactatctgc acctatacaa caaataaatg cagcaactca aaacagtaaa     1320
tatctagatg gagaaacaat aaatggaata ggggcgtcct tacctggtta ttgtactaca     1380
ggatgttcag caacagaaca accttttagt tgtacttcta atgctaatag ctataaatca     1440
agctgtaatc cttcagatac taatcaaaaa attaatgctt tatatgcttt tacacaaact     1500
aatgtaaagg gaaacacggg gaaattagga gtactggcaa gtcttgttcc atatgattta     1560
aatcctaaaa atgtatttgg tgaattagat tcagatacaa ataatgttat cttaaaagga     1620
attcctgcag aaaaagggta ttttttctaat aatgcgcgac ctactgttgt aaaagaatgg     1680
attaatggtg caagtgctgt accactttat tcaggaaata ctttatttat gacggctacg     1740
aatttaacag ctactcaata taaaattaga atacgttatg caaatccaaa ttcagatact     1800
caaatcggtg tacgaattac gcaaaatggt tctctaattt ccaatagtaa tccaccgctt     1860
tatagtacta ctgattcaag tatgagtagt aatttaccac aaaatgtata tgtcacaggg     1920
gaaaatggaa attatacact tctagattta tatagtacta ataatgtttt atcaacagga     1980
gatattacat tacaacttac aggaggaaat caaaaaatat ttattgatcg aatagaattt     2040
atacctacta tg                                                         2052
```

<210> SEQ ID NO 5
<211> LENGTH: 707
<212> TYPE: PRT
<213> ORGANISM: Artificial Sequence
<220> FEATURE:
<223> OTHER INFORMATION: Amino acid coding sequence for a Bacillus
      thuringiensis RX008 variant that is optimized for
      expression in soybean plants.

<400> SEQUENCE: 5

```
Met Ala Asn Lys His Leu Ser Leu Ser Leu Phe Leu Val Leu Leu Gly
 1               5                  10                  15

Leu Ser Ala Ser Leu Ala Ser Gly Arg Met Asp Cys Asn Leu Gln Ser
            20                  25                  30

Gln Gln Asn Ile Pro Tyr Asn Val Leu Ala Ile Pro Val Ser Asn Val
        35                  40                  45

Asn Ala Leu Val Asp Thr Ala Lys Asp Leu Lys Glu Ala Trp Glu Ala
    50                  55                  60

Phe Gln Lys Thr Gly Ser Phe Ser Leu Thr Ala Leu Gln Gln Gly Phe
65                  70                  75                  80

Ser Ala Ser Gln Gly Gly Ala Phe Asn Tyr Leu Thr Leu Leu Gln Ser
                85                  90                  95

Gly Ile Ser Leu Ala Gly Ser Phe Val Pro Gly Gly Thr Phe Val Ala
            100                 105                 110

Pro Ile Val Asn Met Val Ile Gly Trp Leu Trp Pro His Lys Asn Lys
        115                 120                 125
```

```
Thr Ala Asp Thr Glu Asn Leu Ile Lys Leu Ile Asp Glu Ile Gln
        130                 135                 140

Lys Gln Leu Asn Lys Ala Leu Leu Glu Gln Asp Lys Asn Asn Trp Thr
145                 150                 155                 160

Ser Phe Leu Glu Ser Ile Phe Asp Val Ser Asn Thr Val Ser Asn Ala
                165                 170                 175

Met Ile Asp Ala Gln Trp Ser Gly Thr Val Asp Thr Thr Asn Arg Gln
            180                 185                 190

Pro Lys Thr Pro Thr Thr Ser Asp Tyr Leu Asn Val Val Gly Lys Phe
        195                 200                 205

Asp Ser Ala Asp Ser Ala Ile Val Thr Asn Glu Asn Gln Ile Met Asn
210                 215                 220

Gly Asn Phe Asp Val Ala Ala Ser Pro Tyr Phe Val Ile Gly Ala Thr
225                 230                 235                 240

Leu Arg Leu Ser Leu Phe Gln Ser Tyr Ile Lys Phe Cys Asn Asn Trp
                245                 250                 255

Ile Asp Ala Val Gly Phe Asn Pro Ser Asp Ser Asn Thr Gln Lys Ala
            260                 265                 270

Asn Leu Ala Arg Met Lys Gln Thr Met Arg Ile Thr Ile Asn Glu Tyr
        275                 280                 285

Thr Gln Arg Ile Met Lys Val Phe Lys Asp Pro Lys Asn Met Pro Thr
    290                 295                 300

Ile Gly Thr Asn Lys Phe Ser Val Asp Ala Tyr Asn Val Tyr Val Lys
305                 310                 315                 320

Gly Met Thr Leu Asn Val Leu Asp Met Val Ala Ile Trp Pro Ser Leu
                325                 330                 335

Tyr Pro Asn Asp Tyr Thr Ser Gln Thr Thr Leu Glu Gly Thr Arg Val
            340                 345                 350

Thr Phe Ser Asn Met Val Gly Gln Glu Glu Gly Thr Asp Gly Thr Leu
        355                 360                 365

Lys Ile Tyr Asn Thr Phe Asp Ser Ser Ser Phe Gln His Ser Leu Ile
    370                 375                 380

Pro Asn Asn Asn Val Asp Leu Ile Ser Tyr Phe Asn Asp Glu Leu Gln
385                 390                 395                 400

Asn Leu Glu Leu Ala Val Tyr Thr Pro Pro Lys Lys Asp Ser Gly Tyr
                405                 410                 415

Ser Tyr Pro Tyr Gly Phe Val Leu Lys Tyr Ala Asn Ser Lys Tyr Lys
            420                 425                 430

Tyr Gly Asp Ser Asn Asp Pro Glu Ser Leu Gly Gly Leu Ser Thr Leu
        435                 440                 445

Ser Ala Pro Ile Gln Gln Ile Asn Ala Ala Thr Gln Asn Ser Lys Tyr
    450                 455                 460

Leu Asp Gly Glu Thr Ile Asn Gly Ile Gly Ala Ser Leu Pro Gly Tyr
465                 470                 475                 480

Cys Thr Thr Gly Cys Ser Ala Thr Glu Gln Pro Phe Ser Cys Thr Ser
                485                 490                 495

Asn Ala Asn Ser Tyr Lys Ser Ser Cys Asn Pro Ser Asp Thr Asn Gln
            500                 505                 510

Lys Ile Asn Ala Leu Tyr Ala Phe Thr Gln Thr Asn Val Lys Gly Asn
        515                 520                 525

Thr Gly Lys Leu Gly Val Leu Ala Ser Leu Val Pro Tyr Asp Leu Asn
    530                 535                 540
```

-continued

```
Pro Lys Asn Val Phe Gly Glu Leu Asp Ser Asp Thr Asn Asn Val Ile
545                 550                 555                 560

Leu Lys Gly Ile Pro Ala Glu Lys Gly Tyr Phe Ser Asn Asn Ala Arg
            565                 570                 575

Pro Thr Val Val Lys Glu Trp Ile Asn Gly Ala Ser Ala Val Pro Leu
        580                 585                 590

Tyr Ser Gly Asn Thr Leu Phe Met Thr Ala Thr Asn Leu Thr Ala Thr
    595                 600                 605

Gln Tyr Lys Ile Arg Ile Arg Tyr Ala Asn Pro Asn Ser Asp Thr Gln
610                 615                 620

Ile Gly Val Arg Ile Thr Gln Asn Gly Ser Leu Ile Ser Asn Ser Asn
625                 630                 635                 640

Pro Pro Leu Tyr Ser Thr Thr Asp Ser Ser Met Ser Ser Asn Leu Pro
                645                 650                 655

Gln Asn Val Tyr Val Thr Gly Glu Asn Gly Asn Tyr Thr Leu Leu Asp
            660                 665                 670

Leu Tyr Ser Thr Asn Asn Val Leu Ser Thr Gly Asp Ile Thr Leu Gln
        675                 680                 685

Leu Thr Gly Gly Asn Gln Lys Ile Phe Ile Asp Arg Ile Glu Phe Ile
    690                 695                 700

Pro Thr Met
705
```

<210> SEQ ID NO 6
<211> LENGTH: 2124
<212> TYPE: DNA
<213> ORGANISM: Artificial Sequence
<220> FEATURE:
<223> OTHER INFORMATION: Nucleic acid coding sequence for a Bacillus
      thuringiensis RX008 variant that is optimized for
      expression in soybean plants.

<400> SEQUENCE: 6

```
atggccaaca agcacctgtc cctctcccte ttcctcgtgc cctcggcct ctccgcctcc      60 ctcgcctccg gaaggatgga ttgcaacctt cagtctcagc agaacattcc ttacaacgtg    120
ctggccattc ccgtgtccaa cgtgaacgct ctggtcgaca ctgctaagga cctcaaggag    180
gcttgggagg ccttccagaa gacccggtcc ttctctctca gccttgca gcagggattc      240 tctgcatctc aggaggagc cttcaactac ctcacctcgc ttcagtccgg catctccttg     300
gcaggctcct tcgtcccagg aggaaccttc gtcgcaccta tcgtcaacat ggtgattgga    360
tggctgtggc ctcacaagaa caagaccgcc gacaccgaga acctcatcaa actgatcgac    420
gaggagatcc agaagcagct gaacaaggct tgctggagc aggacaagaa caactggact    480
tccttcctcg agtccatctt cgacgtctcc aacaccgtgt ccaacgccat gatcgacgct   540
cagtggtctg gcactgtgga cactaccaac aggcagccta agactcccac tacttccgac   600
tatctcaacg tcgtgggaaa gttcgactcc gcagactctg ccattgtgac caacgagaac  660
cagatcatga acggcaactt cgacgtggct gcctctcctt acttcgtgat cggagctacc   720
ctcagattgt ccctcttcca gtcctacatc aagttctgca acaactggat cgatgctgtg   780
ggcttcaacc cttccgactc taacacccag aaggccaacc tgccaggat gaagcagacc   840 atgaggatca ccatcaacga gtacactcag cgcatcatga aggtgttcaa ggaccccaag   900
aacatgccca ctcgggac caacaagttc tccgttgacg cctacaacgt ctacgtgaaa     960
gggatgaccc tcaacgtgct cgacatggtg gctatctggc catctctcta tcccaacgac   1020
```

-continued

```
tacacttctc agaccactct tgagcagact cgcgtgacct tctccaacat ggtcggacag    1080
gaagagggta ctgacgggac tctcaagatc tacaacacct tcgactcctc ttccttccag    1140
cactccctca ttcccaacaa caacgtggac ttgatctcct acttcaacga cgagctccag    1200
aacctcgagc tcgctgtgta cactcctccc aagaaggact ccggttactc ctacccttac    1260
ggcttcgtgc tcaagtacgc caactctaag tacaagtacg gcgactccaa cgaccctgag    1320
tccttgggag gactctccac actgtccgca cctatccagc agatcaacgc tgctacccag    1380
aactccaagt acctcgacgg tgagaccatc aacggcatcg gagcttccct tccaggctac    1440
tgcactaccg gatgctcagc taccgagcag cctttcagtt gcacctccaa cgccaactcc    1500
tacaagtcct cctgcaaccc ttccgacacc aaccagaaga tcaacgctct ctacgccttc    1560
actcagacca acgtgaaggg taacactggc aagctcggag tgctcgcttc actggtgccc    1620
tacgacctca accctaagaa cgtgttcgga gagttggact ccgacaccaa caacgtgatt    1680
ctcaagggta tccctgccga gaagggctac ttctccaaca acgctcgccc taccgtcgtc    1740
aaggagtgga tcaacggagc ttctgccgtg ccactgtact ctggcaacac cctgttcatg    1800
accgctacca acctcaccgc tacccagtac aagatccgca tacgctacgc caacccaac    1860 tctgacactc agatcggcgt caggatcacc cagaacggct ctctgatctc caactccaac    1920
cctcccttgt actccaccac tgactcctcc atgtcctcca accttcctca gaacgtgtac    1980
gtgaccggcg agaacgggaa ctacactctt ctggacctgt actctaccaa caacgtcctg    2040
tccactggag acatcactct gcagctgaca ggtgggaacc agaagatctt catcgaccgc    2100
attgagttca ttcccaccat gtag                                           2124
```